(12) United States Patent
Yasuura et al.

(10) Patent No.: US 10,976,255 B2
(45) Date of Patent: Apr. 13, 2021

(54) OPTICAL DETECTION METHOD AND OPTICAL DETECTION DEVICE

(71) Applicant: NATIONAL INSTITUTE OF ADVANCED INDUSTRIAL SCIENCE AND TECHNOLOGY, Tokyo (JP)

(72) Inventors: Masato Yasuura, Ibaraki (JP); Makoto Fujimaki, Ibaraki (JP); Hiroki Ashiba, Ibaraki (JP); Takayuki Shima, Ibaraki (JP)

(73) Assignee: NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 244 days.

(21) Appl. No.: 16/097,121

(22) PCT Filed: Feb. 23, 2017

(86) PCT No.: PCT/JP2017/006759
§ 371 (c)(1),
(2) Date: Oct. 26, 2018

(87) PCT Pub. No.: WO2017/187744
PCT Pub. Date: Nov. 2, 2017

(65) Prior Publication Data
US 2019/0154580 A1 May 23, 2019

(30) Foreign Application Priority Data

Apr. 28, 2016 (JP) .............................. JP2016-090662
Dec. 19, 2016 (JP) .............................. JP2016-245113

(51) Int. Cl.
*G01N 21/64* (2006.01)
*G01N 21/51* (2006.01)
(Continued)

(52) U.S. Cl.
CPC ......... *G01N 21/6428* (2013.01); *G01N 21/17* (2013.01); *G01N 21/41* (2013.01);
(Continued)

(58) Field of Classification Search
CPC ........ G01N 21/17; G01N 21/41; G01N 21/51; G01N 21/552; G01N 21/553; G01N 21/64;
(Continued)

(56) References Cited

U.S. PATENT DOCUMENTS

2010/0323355 A1 12/2010 Dittmer
2010/0324828 A1 12/2010 Kahlman et al.
(Continued)

FOREIGN PATENT DOCUMENTS

JP 2002-236258 A 8/2002
JP 2005-077338 A 3/2005
(Continued)

OTHER PUBLICATIONS

Yasuura et al. Scientific Reports, vol. 6:39241, Dec. 19, 2016, pp. 1-7.*
(Continued)

*Primary Examiner* — Maureen Wallenhorst
(74) *Attorney, Agent, or Firm* — Michael Best & Friedrich LLP

(57) ABSTRACT

The invention relates to a method that detects the target substance by measuring a decrease in the optical signal generated by applying a first magnetic field to move the conjugate in the direction parallel to or away from the surface, etc. The invention also relates to an optical detection device wherein a liquid holding part has a sensing plate that can form a near field on a surface with light irradiated from a side of a rear face under a condition of total reflection, the liquid holding part being capable of holding a liquid sample
(Continued)

that has a target substance and a magnetic particle that forms a conjugate with the target substance on the surface of the sensing plate, a light irradiation unit, a light detection unit, and a magnetic field application unit configured to apply a magnetic field to move the conjugate in the direction parallel to or away from the surface, etc.

13 Claims, 10 Drawing Sheets

(51) Int. Cl.
  *G01N 33/543* (2006.01)
  *G01N 21/41* (2006.01)
  *G01N 21/17* (2006.01)

(52) U.S. Cl.
  CPC ............ *G01N 21/51* (2013.01); *G01N 21/64* (2013.01); *G01N 21/6456* (2013.01); *G01N 33/543* (2013.01); *G01N 33/54326* (2013.01)

(58) Field of Classification Search
  CPC ........... G01N 21/6428; G01N 21/6456; G01N 21/648; G01N 33/543; G01N 33/54326
  USPC ....... 436/526, 149, 150, 151, 164, 165, 172, 436/173; 422/82.05, 82.08, 82.09; 435/7.1
  See application file for complete search history.

(56) References Cited

U.S. PATENT DOCUMENTS

| | | |
|---|---|---|
| 2011/0025315 A1 | 2/2011 | Ohtsuka |
| 2011/0065209 A1 | 3/2011 | Heil et al. |
| 2012/0184048 A1 | 7/2012 | Van Ommering et al. |
| 2012/0202194 A1* | 8/2012 | Evers ................. G01N 15/1434 435/5 |
| 2012/0252033 A1 | 10/2012 | Van Zon et al. |
| 2012/0252111 A1 | 10/2012 | Tono et al. |
| 2012/0262565 A1 | 10/2012 | Kahlman et al. |
| 2013/0309779 A1 | 11/2013 | Kasai et al. |
| 2020/0158637 A1* | 5/2020 | Fujimaki ............... G01N 33/543 |

FOREIGN PATENT DOCUMENTS

| | | | |
|---|---|---|---|
| JP | 2010-145408 A | 7/2010 | |
| JP | 2010-530956 A | 9/2010 | |
| JP | 2011-033454 A | 2/2011 | |
| JP | 2013-503352 A | 1/2013 | |
| JP | 2013-024606 A | 2/2013 | |
| JP | 2013-238541 A | 11/2013 | |
| WO | WO-2008/102218 A1 | 8/2008 | |
| WO | WO-2009/081336 A1 | 7/2009 | |
| WO | WO-2011/026030 A1 | 3/2011 | |
| WO | WO-2015/194663 A1 | 12/2015 | |

OTHER PUBLICATIONS

Yasuura et al. Japanese Journal of Applied Physics, vol. 58, Jul. 4, 2019, pp. 071005-1-071005-5.*
Search Report issued in European Application No. 17789033.2, dated Nov. 25, 2019.
Dhesingh Ravi Shankaran et al., "Recent advancements in surface plasmon resonance immunosensors for detection of small molecules of biomedical, food and environmental interest", Sensors and Actuators, ScienceDirect, Oct. 2006, pp. 158-177, vol. B 121, Elsevier B.V., USA.
Makoto Fujimaki et al., Parallel-incidence-type waveguide-mode sensor with spectral-readout setup, Optical Express, May 4, 2015, pp. 10925-10937, vol. 23, No. 9, OSA—The Optical Society, USA.
Claes Nylander et al., "Gas Detection by Means of Surface Plasmon Resonance", Sensors and Actuators, Jul. 1982, pp. 79-88, vol. 3 (1982/83), Elsevier Sequoia, The Netherlands.
Olivier R. Bolduc et al., "High-resolution surface plasmon resonance sensors based on a dove prism", Talanta, Mar. 15, 2009, pp. 1680-1687, vol. 77, Issue 5, Elsevier B.V., USA.
R. Cush et al., "The resonant mirror: a novel optical biosensor for direct sensing of biomolecular interactions Part I: Principle of operation and associated instrumentation", Biosensors & Bioelectronics, 1993, pp. 347-353, vol. 8, Elsevier Science Publishers Ltd.
P.E. Buckle et al., "The resonant mirror: a novel optical sensor for direct sensing of biomolecular interactions Part II: Applications", Biosensors & Bioelectronics, 1993, pp. 355-363, vol. 8, Elsevier Science Publishers Ltd.
R.P. Podgorsek et al., "Optical gas sensing by evaluating ATR leaky mode spectra", Sensors and Actuators, 1997, pp. 349-352, vol. B 38-39, Elsevier Science S.A.
Shinji Hayashi et al., "Fano resonance and plasmon-induced transparency in waveguide-coupled surface plasmon resonance sensors", Applied Physics Express, Iposcience, Jan. 6, 2015, vol. 8, No. 2, The Japan Society of Applied Physics, Japan.
International Search Report issued in Application No. PCT/JP2017/006759, dated May 16, 2017.

* cited by examiner

OPTICAL DETECTION METHOD AND OPTICAL DETECTION DEVICE

TECHNICAL FIELD

The present invention relates to an optical detection method that optically detects a target substance in liquid by using a near field that is generated with the total reflection of light, and such an optical detection device.

BACKGROUND ART

Recently methods have been developed to detect and determine the amount of a micro substance in liquid solution, particularly of biologically relevant substances, such as DNA, RNA, proteins, viruses, and bacterium. As such methods, for example, surface plasmon resonance (SPR) immunoassay, total internal reflection fluorescence microscopy (TIRFM), and surface plasmon-field enhanced fluorescence spectroscopy (SPFS) are cited.

The SPR immunoassay is a method that combines specific selectivity of antigen-antibody reactions with a surface plasmon resonance sensor that is a high-sensitivity refractometer. This method enables real-time and precise detection and quantitative determination of an antigen-antibody binding in enhanced electric field that is generated on the surface of a gold thin film as the total-reflection surface (see Non-Patent Document 1).

The total internal reflection fluorescence microscopy causes total reflection of the incident light at the interface between a specimen and the cover glass or the slide glass to generate an evanescent field, and observes fluorescence using the evanescent field as excitation light while suppressing the background light as noise (see Patent Document 1). This technique can realize super-resolution, and so enables monomolecular observation.

The SPFS causes total reflection of the incident light at the interface between a gold thin layer on the surface of glass in contact with a prism and a liquid sample by means of an optical setup called Kretschmann configuration. This can excite a surface plasmon resonance on the gold thin film, and can form an enhanced electric field on the surface of the gold thin film. This technique obtains excitation light that is the light enhanced near the surface of the gold thin film due to the surface plasmon resonance, and excites fluorescent molecules in the enhanced electric field using the excitation light to generate intense fluorescence, and observes the fluorescence while having less background light (see Patent Document 2).

Non Patent Documents 2 to 8, for example, describe well-known methods of generating enhanced electric field from the total reflection of light to obtain enhanced electric field. The present inventors have reported such a method in Non-Patent Document 2. The method prepares a sensing plate stacking a silicon layer and a $SiO_2$ layer from the below on a silica glass substrate and disposing the sensing plate on a trapezoidal prism made of silica glass, and applies light through the prism under the condition of total reflection on the surface of the sensing plate to obtain enhanced electric field.

Non Patent Document 3 discloses a method of generating surface plasmon resonance using Kretschmann configuration to obtain an enhanced electric field. Non Patent Document 4 discloses a method of using a dove prism as the prism in the Kretschmann configuration and applying light to the prism to generate a surface plasmon resonance and obtain an enhanced electric field. Non Patent Documents 5 and 6 disclose a method of obtaining an enhanced electric field using a resonant mirror. Non Patent Document 7 discloses a method of forming a structure called a leaky mode sensor by stacking a metal layer and a transparent dielectric layer in this order on a prism and applying light through the prism to obtain an enhanced electric field on the surface of the dielectric layer. Non Patent Document 8 discloses a method of forming a metal layer on a prism and stacking two types of transparent dielectric layers having different indexes of refraction one by one on the metal layer to obtain a more enhanced electric field than that of the leaky mode sensor.

Patent Documents 3 and 4 disclose a method of forming the shape of a prism in a channel to generate surface plasmon resonance and obtaining enhanced electric field by generating a surface plasmon resonance on the bottom or the lateral face of the channel.

Searching of prior-art documents relating to the present invention shows a known method of using magnetic particles as labels to promote the adsorption or access of a target substance to a detector plane for measurement in a shorter time (Patent Documents 5 and 6). The techniques described in Patent Documents 5 and 6 apply a magnetic field to a conjugate of a magnetic label, a photoresponsive label and a target substance to attract it to a localized region and irradiate a predetermined region including this localized region with excitation light so as to remove a signal from a photoresponsive label that does not form a conjugate with the target substance and the magnetic label for detection.

PRIOR ART DOCUMENTS

Patent Documents

Patent Document 1: JP 2002-236258 A
Patent Document 2: WO 2015/194663
Patent Document 3: JP 2013-24606 A
Patent Document 4: JP 2010-145408 A
Patent Document 5: JP 2011-33454 A
Patent Document 6: JP 2005-77338 A Non Patent Documents Non Patent Document 1: Sensors and Actuators B 121 (2007) 158-177
Non Patent Document 2: M. Fujimaki et al. Optics Express, Vol. 23 (2015) pp. 10925-10937
Non Patent Document 3: C. Nylander et al. Sensors and Actuators, Vol. 3 (1982/83) pp. 79-88
Non Patent Document 4: O. R. Bolduc et al. Talanta, Vol. 77 (2009) pp. 1680-1687
Non Patent Document 5: R. Cush et al. Biosensors and Bioelectronics, Vol. 8 (1993) pp. 347-353
Non Patent Document 6: P. E. Buckle et al. Biosensors and Bioelectronics, Vol. 8 (1993) pp. 355-363
Non Patent Document 7: R. P. Podgorsek et al. Sensors and Actuators, B 38-39 (1997) pp. 349-352
Non Patent Document 8: S. Hayashi et al. Applied Physics Express Vol. 8, 022201 (2015)

SUMMARY OF THE INVENTION

Problems to be Solved by the Invention

Among these conventional methods of detecting a target substance using a near field, a method using magnetic particles for enrichment of a target substance on the detector plane has a problem of deterioration in sensitivity of detection because an optical signal from a labeled substance or magnetic particles that are adsorbed to the detector plane in a non-specific manner becomes noise. In this way, conventional methods have a problem of deterioration in sensitivity of detection resulting from the noise due to a labeled substance or magnetic particles. The methods have other factors as well of noise, such as scattered light due to dirt and scratches on the surface of a sensing plate, autofluorescence from a material of a sensing plate, and a non-specific adsorption of contaminants to the surface of a sensing plate, which degrades the sensitivity of detection.

Unfortunately promotion of the enrichment of a target substance on the surface of a sensing plate using magnetic particles causes enrichment of unbound magnetic particles on the surface of the sensing plate at the same time, which results in an increase of the noise source.

To solve these problems, the present invention aims to provide an optical detection method that optically detects a target substance using a near field and such a device. These method and device can remove influences from the noise due to labeled substances and magnetic particles that are adsorbed to a surface of a sensing plate in a non-specific manner, the noise due to dirt and scratches on the surface, the noise due to autofluorescence of a sensing plate, and the noise due to non-specific adsorption of contaminants to the surface, and so enable high-sensitive and high-speed detection of the target substance.

Means for Solving the Problems

To achieve the said aim, the present invention has the following configuration.

(1) An optical detection method for a target substance that detects fluorescence or scattered light as an optical signal from a conjugate comprising the target substance on a surface of a sensing plate in a near field, comprising: detecting the target substance by measuring a decrease in or a movement of the optical signal due to a conjugate moving step, wherein the conjugate comprises at least the target substance bonding with a magnetic particle, and the conjugate moving step is implemented by any one of the steps of: a first conjugate moving step of applying a first magnetic field such that the conjugate moves in a direction parallel to the surface or away from the surface or such that orientation of the conjugate changes; and a second conjugate moving step of drawing the conjugate on the surface by applying a second magnetic field from a magnetic field application unit disposed on a side of a rear face of the sensing plate, and moving the magnetic field application unit in a direction having a vector component parallel to an in-plane direction of the surface of the sensing plate while applying the second magnetic field so as to move the conjugate in accordance with the movement of the magnetic field application unit or change the orientation of the conjugate.

(2) The optical detection method according to the said (1), wherein the decrease in the optical signal results from the conjugate moving away from the surface by applying the first magnetic field.

(3) The optical detection method according to the said (1) or (2), wherein after the conjugate settles out close to the surface due to gravitational sedimentation, the conjugate is moved by the first conjugate moving step.

(4) The optical detection method according to any one of the said (1) to (3), wherein after the conjugate is drawn close to the surface by applying a drawing magnetic field, the conjugate is moved by the first conjugate moving step.

(5) The optical detection method according to the said (4), wherein the step of applying the drawing magnetic field and the first conjugate moving step are alternately conducted a plurality of times.

(6) The optical detection method according to any one of the said (1) to (5), wherein the conjugate comprises two or more the magnetic particles bonding with the target substance.

(7) The optical detection method according to any one of the said (1) to (6), wherein the conjugate comprises the target substance bonding with a labeled substance that emits fluorescence or scattered light in the near field.

(8) The optical detection method according to any one of the said (1) to (7), wherein the conjugate comprises the target substance bonding with a weight substance.

(9) The optical detection method according to any one of the said (1) to (8), wherein the surface is chemically treated to suppress adsorption of the conjugate.

(10) An optical detection device comprising: a liquid holding part comprising a sensing plate that can form a near field on a surface with light irradiated from a side of a rear face under a condition of total reflection, the liquid holding part being capable of holding a liquid sample comprising a target substance and a magnetic particle that forms a conjugate with the target substance on the surface of the sensing plate; a light irradiation unit configured to irradiate light from the side of the rear face of the sensing plate under the condition of total reflection; a light detection unit disposed on a side of the surface of the sensing plate, the light detection unit being configured to detect fluorescence or scattered light emitted from the conjugate at a detection region on the surface and in the near field; and a magnetic field application unit comprising any one of a first magnetic field application unit configured to apply a first magnetic field such that the conjugate moves in a direction parallel to the surface or away from the surface or such that orientation of the conjugate changes, and a second magnetic field application unit disposed on the side of the rear face of the sensing plate, the second magnetic field application unit being configured to be capable of drawing the conjugate in the sample that is introduced on the surface of the sensing plate toward the surface of the sensing plate by applying a magnetic field, and move the conjugate in a direction having a vector component parallel to an in-plane direction of the surface of the sensing plate or change orientation of the conjugate while applying the magnetic field.

(11) The optical detection device according to the said (10), wherein the magnetic field application unit comprises the first magnetic field application unit, and comprises a drawing magnetic field application unit configured to apply a drawing magnetic field to draw the conjugate toward the surface.

(12) The optical detection device according to the said (10) or (11), wherein the light detection unit is a device configured to acquire a state of the detection region comprising the fluorescence or the scattered light as a two-dimensional image.

(13) The optical detection device according to any one of the said (10) to (12), wherein the sensing plate comprises a laminate structure in which a light-transmissive substrate and a metal layer that generates surface plasmon resonance are stacked in this order from the rear face to the surface.

(14) The optical detection device according to any one of the said (10) to (12), wherein the sensing plate comprises a laminate structure in which a light-transmissive substrate, a metal layer or a semiconductor layer, and a dielectric layer made of a light-transmissive dielectric material are stacked in this order from the rear face to the surface.

(15) The optical detection device according to any one of the said (10) to (14), wherein the surface suppresses adsorption of the conjugate.

Advantageous Effect of the Invention

The present invention can clearly distinguish an optical signal from a conjugate comprising a target substance from noise, such as noise due to labeled substances and magnetic particles that are adsorbed to the surface of a sensing plate in a non-specific manner, noise due to dirt and scratches on the surface, noise due to autofluorescence of the sensing plate, and the noise due to non-specific adsorption of contaminants to the surface, and so can greatly improve the sensitivity of detection. External force comprising the application of a magnetic field can move the conjugate, and so the detection time can be shortened.

The present invention may apply a drawing magnetic field prior to the application of the first magnetic field or may apply a drawing magnetic field and the first magnetic field alternately. Such cases enable more sensitive and higher-speed detection.

MODE FOR CARRYING OUT THE INVENTION

Figure 1:
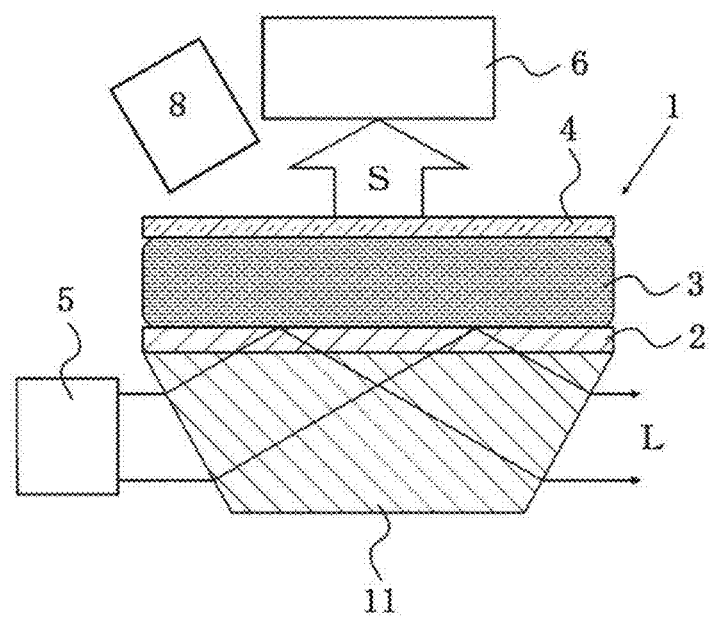
FIG. 1 is a schematic view of a basic optical detection device comprising a magnetic-field applying means of one embodiment of the present invention.

The following describes embodiments of the present invention.

To optically detect a micro substance with a near field on the surface of a sensing plate, the present inventors have focused on the technique of using magnetic particles to manipulate the micro substance. As a result of the keen effort to develop the technique, the present inventors have come up with a new idea of moving a target substance binding with a magnetic particle to the outside of a near field to cause a decrease in optical signal (comprising disappearance) and detecting such a decrease so as to detect the target substance. The present inventors have come up with other ideas of, instead of moving a target substance binding with a magnetic particle to the outside of a near field, moving the target substance within a near field to generate a decrease in optical signal and detecting such a decrease in optical signal or such a movement to detect the target substance, and of detecting a change in orientation of a target substance binding with a magnetic particle to detect the target substance.

An optical detection method of the present invention detects fluorescence or scattered light as an optical signal from a conjugate comprising a target substance on the surface of a sensing plate using a near field to detect the target substance, and the conjugate used comprises at least the target substance bonding with a magnetic particle. The method comprises a conjugate moving step that is implemented by any one of the steps of: a first conjugate moving step of applying a first magnetic field such that the conjugate moves in a direction parallel to or away from the surface or the orientation of the conjugate changes, and a second conjugate moving step of drawing the conjugate toward the surface by applying a second magnetic field from the magnetic field application unit disposed on the side of the rear face of the sensing plate, and moving the magnetic field application unit in the direction having a vector component parallel to the in-plane direction of the surface of the sensing plate while applying the second magnetic field thereto so as to move the conjugate in accordance with the movement of the magnetic field application unit or change the orientation of the conjugate. The method then measures a decrease in the optical signal or the movement of the optical signal due to the conjugate moving step to detect the target substance.

In this description, a "movement of optical signal" is a concept that covers the movement of an optical signal along with the movement of the conjugate and a change in the optical signal due to a change in orientation of the conjugate. A "movement of a conjugate" is a concept that covers the movement of the conjugate and a change in orientation of the conjugate.

An optical detection device of the present invention comprises a liquid holding part, a light irradiation unit, a light detection unit, and a magnetic field application unit.

(Liquid Holding Part)

The liquid holding part comprises a sensing plate, and holds a liquid sample comprising a target substance to be introduced and a magnetic particle to be added to the sample and that bonds with the target substance to form a conjugate on the surface of the sensing plate.

The samples include blood, saliva, urine, medicines, environment water, and clean and sewage water, etc. The target substances include DNA, RNA, proteins, viruses, bacteria and contaminated substances, etc. The sample may be any liquid that can be measured with the optical detection device, and is not limited to the above examples. The target substance is not limited especially, and may be any substance that is included in the sample and can be detected about the presence, or that can be measured with the content thereof.

The sensing plate may be configured so that a sample can be introduced on the surface and it can form a near field on the surface with light irradiated from the rear surface under the condition of total reflection. The structure of the sensing plate is not limited especially, and can be selected as needed depending on the purpose. The sensing plate may comprise a single layer or a laminate for enhanced electric field. The sensing plate has a face as the total-reflection face, which is preferably an optically flat face to generate total reflection.

For the configuration of a sensing plate formed of a single layer, when irradiated light is total-reflected at the surface of the single layer as the total-reflection face, an evanescent field will be generated close to the surface. Such a phenomenon occurs generally irrespective of materials that have a light-transmissive property of transmitting the irradiated light through the single layer. The material of the single layer therefore is not limited especially, and can be selected as needed from well-known materials to form a sensing plate having a light-transmissive property.

For the configuration of a sensing plate formed of a laminate, the laminate is not limited especially. For instance, a well-known sensing plate as those described in Patent Documents 2 to 5 and Non Patent Documents 2 to 8, which are for enhanced electric field, can be used.

When the sensing plate is configured to stack a light-transmissive substrate and a metal layer that generates surface plasmon resonance in this order from the rear face to the surface of the sensing plate, light irradiated from the rear face of the sensing plate excites surface plasmon resonance on the surface of the metal layer, whereby an enhanced electric field can be obtained close to the surface of the sensing plate. This results in increased intensity of an optical signal emitted from a conjugate comprising a target substance and so can improve the sensitivity. A structure and a forming material of the laminate to excite the surface plasmon resonance are not limited especially, and well-known laminates as described in Non-Patent Documents 3 and 4, for example, can be used.

When the sensing plate is configured to stack a light-transmissive substrate, a metal layer made of a metal material or a semiconductor layer made of a semiconductor material, and a dielectric layer made of a light-transmissive dielectric material in this order from the rear face to the surface of the sensing plate, light irradiated from the rear face of the sensing plate excites a waveguide mode in the dielectric layer, whereby an enhanced electric field can be obtained close to the surface of the sensing plate. This results in increased intensity of an optical signal emitted from a target substance and so can improve the sensitivity.

A structure and a forming material of the laminate to excite a waveguide mode are not limited especially, and a well-known laminate as described in Non-Patent Document 2, for example, can be used.

In this description, a "near field" refers to any one of an evanescent field and an enhanced electric field. Both of these evanescent field and enhanced electric field are formed close to the surface of the sensing plate only, and have a property of sharply attenuating with distance from the surface of the sensing plate.

A forming material of the light-transmissive substrate is not limited especially, and can be selected as needed depending on the purpose from well-known light-transmissive dielectric materials, such as glass and plastics.

A structure of the liquid holding part is not limited especially, and can be selected as needed depending on the purpose. For instance, the liquid holding part may be the sensing plate itself. Another structure may comprise a light-transmissive member, such as a cover glass, and a sensing plate configured to sandwich a sample therebetween, and may hold the liquid layer of the sample on the surface of the sensing plate. Alternatively, the liquid holding part may comprise a well-known liquid cell or a well-known liquid channel disposed on the surface of a sensing plate.

Preferably the liquid holding part may comprise an introduction part of a sample and a hollow that defines a space comprising at least a region to form a near field on the surface of the sensing plate with the sensing plate and a cover of the sensing plate, and at least a part between a detection region on the surface of the sensing plate and the light detection unit has a light-transmissive property. Such a liquid holding part having a hollow can easily introduce a sample by drawing the sample from the introduction part to the hollow, and can introduce a certain amount of the sample stably in accordance with the capacity of the hollow.

The liquid holding part may have a plurality of subdivided regions to hold the sample for multi-channeling.

(Light Irradiation Unit)

The light irradiation unit can irradiate light from the rear face of the sensing plate under the condition of total reflection.

The light source of the light irradiation unit is not limited especially, and can be selected as needed depending on the purpose. Examples of the light source include well-known lamps, LEDs, and lasers, etc. To detect a target substance, the present invention is based on the principle to irradiate light from the rear face of the sensing plate under the condition for total reflection so as to form a near field close to the surface, so that the near field can generate fluorescence or scattered light from a conjugate comprising the target substance. To this end, the light irradiation unit simply has a role of irradiating light from the rear face of the sensing plate under the condition for total reflection, and any light source can be selected as long as it can play such a role.

When a radiant light source, such as lamps and LEDs, is used, the light in all directions to be applied to the rear face of the sensing plate from the radiated light has to satisfy the condition for total reflection so as to avoid the leakage of the irradiated light from the surface of the sensing plate. Thus, when a radiant light source is used, a guide unit such as a collimator lens that regulates the direction of the irradiated light to a specific direction may be used.

When fluorescence from the conjugate comprising a target substance is used as an optical signal, a monochromatic light source having a wavelength that can excite fluorescence is preferably used. Alternatively light from a light source having a wide wavelength range, such as lamps and LEDs, may be allowed to pass through an optical filter, such as a bandpass filter, to be monochromatic light, and the light having a wavelength that can excite fluorescence only may be extracted and be applied from the rear face of the sensing plate.

For the sensing plate having the surface and the rear face that are parallel to each other, light irradiated from the rear face is not total-reflected if liquid is present on the surface. In such a case, a diffraction grating may be formed at a part of the rear face of the sensing plate. Then the sensing plate may be configured so that the light irradiated on the diffraction grating at a specific angle can be diffracted with the diffraction grating and be introduced into the sensing plate and such light introduced into the sensing plate is irradiated on the surface under the condition for total reflection so as to form a near field close to the surface. The surface and the rear face of the sensing plate may not be parallel to each other. Alternatively light irradiated from a light source may be applied to the rear face of the sensing plate via a well-known prism. Such a prism may be optically attached to the rear face of the sensing plate with oil to adjust the refractive index or with optical adhesive, for example. The prism may be made of the same forming material as the light-transmissive substrate or the single layer of the sensing plate. In such a case, the sensing plate and the prism may be integrally formed. A structure having the function of a prism for a liquid channel as disclosed in Patent Documents 3 and 4 also may be used.

(Light Detection Unit)

The light detection unit is disposed on the side of the surface of the sensing plate, and has a region on the surface as a detection region. When the light is irradiated, the light detection unit can detect an optical signal emitted from a conjugate comprising a target substance. The light detection unit is not limited especially, and can be selected as needed depending on the purpose. Examples of the light detection unit include well-known photodetectors, such as a photodiode and a photomultiplier. When the light detection unit can acquire the information on an optical signal as two-dimensional image information, positional information on the optical signal in the two-dimensional image information that appears light spots, size information that can be observed two-dimensionally, information on an increase/decrease of the intensity of the optical signal at light spots can be observed in chronological order. Thereby the light spots can be distinguished about whether they result from a target substance or indicate the information relating to a target substance, or whether they indicate the information that does not relate to a target substance, such as contaminants, fluctuation in the output from the light source and scratches on the surface of the sensing plate. To obtain such two-dimensional image information, as the light detection unit, an imaging device may be selected. The imaging device is not limited especially, and can be selected as needed depending on the purpose. Examples of the imaging device include well-known image sensors, such as a CCD image sensor and a CMOS image sensor.

(Magnetic Field Application Unit)

The magnetic field application unit is formed with any one of the following a first magnetic field application unit and a second magnetic field application unit.

<First Magnetic Field Application Unit>

The first magnetic field application unit moves a conjugate in the direction parallel to the surface of the sensing plate or in the direction away from the surface, or changes the orientation of the conjugate. The first magnetic field application unit can apply an away magnetic field that moves a conjugate of a target substance and a magnetic particle away from the surface of the sensing plate or a parallel-movement magnetic field that applies a magnetic force to move the conjugate in the vicinity of the surface and in parallel with the surface. The conjugate can emit an optical signal due to fluorescence or scattered light only within a near field. The intensity of the electric field in the near field attenuates with distance from the surface of the sensing plate. This means that as the away magnetic field applied moves the conjugate away from the surface, the optical signal attenuates. When the conjugate is distant from the surface beyond a distance where the intensity of the electric field in the near field can be considered as zero, the optical signal of the conjugate disappears. When the light detection unit using an imaging device can acquire two-dimensional image information, an optical signal emitted from a conjugate that moves in the vicinity of the surface due to the first magnetic field applied can be measured over time as a movement of the optical signal. The present invention detects such attenuation (including disappearance) or such a movement (including attenuation and disappearance) of an optical signal to detect a target substance. The first magnetic field application unit is not limited especially as long as it can generate a magnetic field that can move a conjugate away from the surface of the sensing plate or move a conjugate in the vicinity of the surface, and can be selected as needed depending on the purpose. The first magnetic field application unit may use at least one of a well-known electromagnet and such a permanent magnet. The direction of applying the first magnetic field also is not limited especially as long as it can move the conjugate away from the surface of the sensing plate, move the conjugate in parallel with and in the vicinity of the surface, or change the orientation of the conjugate, and can be set as needed depending on the purpose.

<Second Magnetic Field Application Unit>

The second magnetic field application unit is disposed on the side of the rear face of the sensing plate. The second magnetic field application unit applies a magnetic field to draw the conjugate in the sample that is introduced on the surface of the sensing plate toward the surface of the sensing plate, and moves the conjugate in the direction having a vector component parallel to the in-plane direction of the surface of the sensing plate or changes the orientation of the conjugate while applying the magnetic field thereto.

The second magnetic field application unit is not limited especially as long as it is as stated above, and can be selected as needed depending on the purpose. For instance, the second magnetic field application unit can use a well-known electromagnet or such a permanent magnet. For instance, the second magnetic field application unit holds the electromagnet or the permanent magnet on a slide member, and may be controlled about the movement to have an initial state where the electromagnet or the permanent magnet is located in the vicinity of a region (detection region) irradiated with the light from the light irradiation unit on the side of the rear face of the sensing plate, and a state where the electromagnet or the permanent magnet is shifted in the direction having a vector component parallel to the in-plane direction of the surface of the sensing plate. When the electromagnet is used, the electromagnet is continuously or intermittently energized during the control of the movement. During the control of the movement, the intensity of energizing may change.

A plurality of such electromagnets or permanent magnets may be disposed to control the application state of the magnetic field at each of the magnets, from which the same effect as that from the configuration holding the electromagnet or the permanent magnet on the slide member can be obtained.

The configuration of the second magnetic field application unit is not limited especially, and it may have an incomplete annular shape, such as having a through hole or having a U-letter shape, or may include a plurality of members that are arranged in an annular or an incomplete annular shape.

(Magnetic Particle)

A magnetic particle bonds with a target substance to form a conjugate. Receiving a magnetic force from the magnetic field application unit, the magnetic particle acts so as to move the target substance away from the surface of the sensing plate or to move the target substance in the vicinity of the surface. Magnetic particles are not limited especially, and can be selected as needed depending on the purpose. For instance, well-known magnetic beads can be used.

A method for binding a magnetic particle with a target substance is not limited especially as long as it can bond both of them physically or chemically, can be selected as needed depending on the purpose, and for instance, physical adsorption, antigen-antibody reaction, DNA hybridization, biotin-avidin bond, chelate bond, and amino bond can be used. Physical adsorption bonds a magnetic particle with a target substance using an electrostatic bonding force, such as hydrogen bond.

Physical adsorption has the advantageous effect of facilitating the bonding because no special treatment is required for magnetic particles. Magnetic particles, however, typically have low selectivity because they do not adsorb only to a target substance in a specific manner. That is, magnetic particles may bond with contaminants other than a target substance in the sample, and if the contaminants emit an optical signal similar to the target substance, the target substance cannot be distinguished from the contaminants.

When a magnetic particle bonds with a target substance through a reaction having high specificity, such as an antigen-antibody reaction, the magnetic particle selectively bonds with the target substance only. This method therefore has the advantageous effect of distinguishing contaminants and the target substance for detection. In this case, however, when the target substance is an antigen, such as viruses, an antibody corresponding to the viruses has to bond with the magnetic particle beforehand.

(Labeled Substance)

In the present invention, a labeled substance, which generates an optical signal, such as fluorescence or scattered light in a near field, may bond with a target substance. Such a labeled substance is particularly effective when an optical signal from the target substance is weak and it is difficult to detect such an optical signal, and the labeled substance plays a role of emitting a strong optical signal instead of the target substance. The labeled substance is not limited especially, and can be selected as needed depending on the purpose. For instance, well-known fluorescent substances or substances that scatter light may be used. The fluorescent substances include well-known fluorescent substances, such as fluorescent dye or quantum dots. Substances that scatter light include nanoparticles, such as polystyrene beads and gold nanoparticles.

A method for bonding a labeled substance with a target substance is not limited especially as long as it can bond both of them physically or chemically and can be selected as needed depending on the purpose, and for instance, physical adsorption, antigen-antibody reaction, DNA hybridization, biotin-avidin bond, chelate bond, and amino bond can be used. When dye is used for the labeled substance, dying of the target substance with the dye also is an effective means to bond the labeled substance with the target substance.

Physical adsorption bonds a labeled substance with a target substance using an electrostatic bonding force, such as hydrogen bond. Physical adsorption has the advantageous effect of facilitating the bonding because no special treatment is required for the labeled substance. A labeled substance, however, typically has low selectivity because it does not adsorb only to a target substance in a specific manner. That is, a labeled substance may bond with contaminants other than a target substance in the sample, and the contaminants may emit an optical signal as noise.

When a labeled substance bonds with a target substance through a reaction having high specificity, such as an antigen-antibody reaction, the labeled substance selectively bonds with the target substance only. This method therefore has the advantageous effect of distinguishing contaminants and the target substance for detection. In this case, however, when the target substance is an antigen, such as viruses, an antibody corresponding to the viruses has to bond with the labeled substance beforehand.

When both of the magnetic particle and the labeled substance bond with the target substance for detection, any one of these bonds preferably is a bond through a specific reaction with the target substance. This is because, if both of the bonds occur in a non-specific manner, both of the magnetic particle and the labeled substance may bond with contaminants in the sample at the same time. This may make it impossible to distinguish between the target substance and the contaminants.

When the magnetic particle emits an optical signal, such as fluorescence or scattered light, the magnetic particle may double as the labeled substance. This is preferable because the procedure of bonding with the labeled substance can be omitted. In this case the bonding between the magnetic particle and the labeled substance is preferably a specific bond between them. This is because, if the bonding between them occurs in a non-specific manner, the magnetic particle may bond with contaminants in the sample as well and may emit an optical signal. This may make it impossible to distinguish between the target substance and the contaminants.

(Drawing Magnetic Field to Draw Toward Surface of Sensing Plate or Gravitational Sedimentation)

In the present invention, when the target substance is detected by detecting fluorescence or scattered light as an optical signal from a conjugate comprising a target substance on a surface of a sensing plate in a near field, the target substance is detected by measuring a decrease in or a movement of the optical signal due to a conjugate moving step, wherein the conjugate moving step is implemented by any one of the steps of: a first conjugate moving step of applying a first magnetic field such that the conjugate moves away from the surface or moves in the vicinity of the surface and in the direction parallel to the surface, or the orientation of the conjugate changes, and a second conjugate moving step of drawing the conjugate on the surface by applying a second magnetic field from the magnetic field application unit disposed on the side of a rear face of the sensing plate, and moving the magnetic field application unit in the direction having a vector component parallel to the in-plane direction of the surface of the sensing plate while applying the second magnetic field thereto so as to move the conjugate in accordance with the movement of the magnetic field application unit or change the orientation of the conjugate. That is, the conjugate is detected by applying the first magnetic field to move the conjugate away from the surface of the sensing plate or move the conjugate in the vicinity of the surface and in the direction parallel to the surface or to change the orientation of the conjugate, or by applying the second magnetic field with the magnetic field application unit to move the conjugate in accordance with the movement of the magnetic field application unit or to change the orientation of the conjugate. In such a detection mechanism, the conjugate has to be present in the region where a near field is generated prior to the conjugate moving step.

Typically micro substances, such as DNA, proteins and viruses, are uniformly dispersed in solution. The region where a near field is generated, however, is located from a few hundreds nm to a few μm from the surface of the sensing plate. Therefore if the sample to be introduced into the liquid holding part is thicker than this region, the number of the conjugates present in the near field is limited to a small portion of the total number of the conjugates included in the introduced sample prior to the application of the first magnetic field. To avoid this, as many conjugates as possible are preferably brought closer to the surface of the sensing plate prior to the application of the first magnetic field so that the conjugates can be within the region where the near field is generated. To bring the conjugates closer to the surface of the sensing plate in this way, the present invention performs at least one of settling-out of the conjugates by gravitational sedimentation and drawing of the conjugates toward the surface of the sensing plate by applying a drawing magnetic field.

For the configuration of the optical detection device such that the surface of the sensing plate is the bottom of the liquid holding part, when the conjugates are heavy enough for gravitational sedimentation, the conjugates are drawn to the surface of the sensing plate due to gravitational sedimentation within a certain period of time. With this configuration, the first magnetic field is applied after the certain period of time since the pouring of a sample into the liquid holding part, whereby more conjugates can contribute to the detection, so that a decrease in optical signal or a movement of the optical signal can be observed more. That is, this enables more sensitive detection of a target substance. Note here the certain period of time depends on the size or the weight of the conjugates, and so it is difficult to determine this period of time as a specific value. For a quick detection, this is preferably within one hour.

When the conjugates are light in weight, it takes time for the gravitational sedimentation. In such a case, the conjugate preferably bonds with a weight substance as weight to speed up the gravitational sedimentation. The weight substance is not limited especially and can be selected as needed depending on the purpose, and for instance, well-known gold nanoparticles can be used. A method for bonding conjugates with the weight substance is not limited especially as long as it can bond both of them physically or chemically, and can be selected as needed depending on the purpose, and for instance, physical adsorption, antigen-antibody reaction, DNA hybridization, biotin-avidin bond, chelate bond, and amino bond can be used.

The optical detection device effectively may comprise a drawing magnetic field application unit that can apply a drawing magnetic field so that a magnetic force acts in the direction of drawing the conjugate toward the surface of the sensing plate. This configuration is preferable because the drawing magnetic field application unit draws the magnetic particle of the conjugate toward the surface of the sensing plate, and so the bonding of another substance with the conjugate to bring the conjugate toward the surface of the sensing plate is not required. Following the application of the drawing magnetic field, a first magnetic field, such as an away magnetic field, may be applied, whereby more conjugates can contribute to the detection, so that a decrease in optical signal or a movement of the optical signal can be observed more.

The application of the drawing magnetic field and the application of the first magnetic field (the first conjugate moving step as stated above) may be alternately and repeatedly performed a plurality of times (hereinafter this is called "alternate application of magnetic field"). Such alternate application of magnetic field allows the conjugates to move into and out of the region generating a near field repeatedly, thereby observation of a decrease and an increase of the optical signal is repeated. Thus, it is possible to improve the accuracy of the detection. The alternate application of magnetic field may be performed periodically, and a well-known lock-in amplifier may be applied to the frequency, thereby it is possible to amplify the signal and improve the sensitivity.

(Mixing of Sample)

To measure a target substance with the optical detection device, magnetic particles are added to the sample. A labeled substance and a weight substance also are added as needed. Typically magnetic particles, a labeled substance and a weight substance are dispersed in solution for storage or are stored in the powder form. They are mixed with a sample before use. A method for the mixing is not limited especially and can be selected as needed depending on the purpose. For instance, (1) a method mixing magnetic particles, a labeled substance, and a weight substance after pouring a sample into the liquid holding part, (2) a method in which after pouring magnetic particles, a labeled substance and a weight substance into the liquid holding part, a sample is poured into the liquid holding part, and (3) a method in which after mixing a sample, magnetic particles, a labeled substance and a weight substance (hereinafter this is called "mixing beforehand"), the mixture is poured into the liquid holding part can be used. In the case of the mixing beforehand, the magnetic particles may be collected with a magnet through the vessel to wash the inside of the vessel, whereby substances other than the magnetic particles and the conjugates can be easily removed, and the conjugates can be enriched. This is preferable because more accurate and sensitive detection is enabled.

(Surface Treatment of Sensing Plate)

The surface of the sensing plate may be chemically surface-treated to suppress adsorption of the target substance, the magnetic particles, the labeled substance and the weight substance that make up the conjugates. Such a surface treatment is preferable because the conjugates can move away from the surface of the sensing plate by application of the first magnetic field, such as an away magnetic field or can move in the vicinity of the surface without being immobilized at the surface of the sensing plate. A method for the surface treatment is not limited especially, and can be selected as needed depending on the purpose. For instance, various types of blocking methods can be used to suppress adsorption of proteins. Examples of the blocking include a method using polyethyleneglycol, a method using ethanolamine and a method using skim milk, etc. The surface treatment, which can suppress adsorption of the conjugates to the surface of the sensing plate, enables stable and precise detection.

The following describes examples of the optical detection device and the optical detection method in details, with reference to the drawings.

FIG. 1 shows a basic example of the optical detection device in one embodiment of the present invention. The optical detection device 1 comprises a sensing plate 2, a cover glass 4, a light source 5, a light detection unit 6, and a first magnetic field application unit 8. The cover glass 4 is disposed so that a mixture solution 3 of a sample containing a target substance, magnetic particles, a labeled substance and a weight substance (the labeled substance and the weight substance may not be included) is sandwiched between the cover glass and the sensing plate 2 and so that a liquid layer of the mixture solution 3 is held on the surface of the sensing plate 2. The light source 5 (this may be called a "light irradiation unit") is disposed so that it can apply light L from the side of the rear face of the sensing plate 2 under the condition of total reflection via a prism 11 that is optically attached to the rear face of the sensing plate 2. The light detection unit 6 is disposed on the side of the surface of the sensing plate 2, and has a region on the surface as a detection region. When the light L is irradiated, the light detection unit can detect an optical signal S emitted from the conjugates. The first magnetic field application unit 8 applies an away magnetic field to move the conjugates away from the surface of the sensing plate 2 or a parallel-movement magnetic field to move the conjugates in the vicinity of the surface and in the direction parallel to the surface. The sensing plate 2 and the cover glass 4 define a liquid holding part. The optical detection device 1 of FIG. 1 comprises the prism 11 to irradiate the light L from the side of the rear face of the sensing plate 2 under the condition of total reflection. Instead of the prism 11, another sensing plate having a diffraction grating on the rear face may be used for this purpose.

In this embodiment of the present invention, the first magnetic field application unit 8 moves the conjugates away from the surface of the sensing plate or moves the conjugates in the vicinity of the surface and in the direction parallel to the surface, or changes the orientation of the conjugates to generate a decrease (including disappearance) of the optical signal S or the movement of the optical signal S. This embodiment then detects such a decrease or the movement to detect the target substance. Note here that detection of a target substance denotes determining the presence or not of the target substance, measuring the quantity of the target substance and real-time observation of the target substance, for example.

In FIG. 1, the sensing plate 2 is located under the mixture solution 3. Instead, the sensing plate 2 may be disposed above or lateral to the mixture solution 3. When the conjugates are to be drawn to the surface of the sensing plate by gravitational sedimentation, the sensing plate 2 has to be disposed under the mixture solution 3. On the other hand, when the sensing plate 2 are disposed above or lateral to the mixture solution 3, it is possible to reduce non-specific adsorption of substances other than the target substance to the surface of the sensing plate due to gravitational sedimentation.

Figure 2:
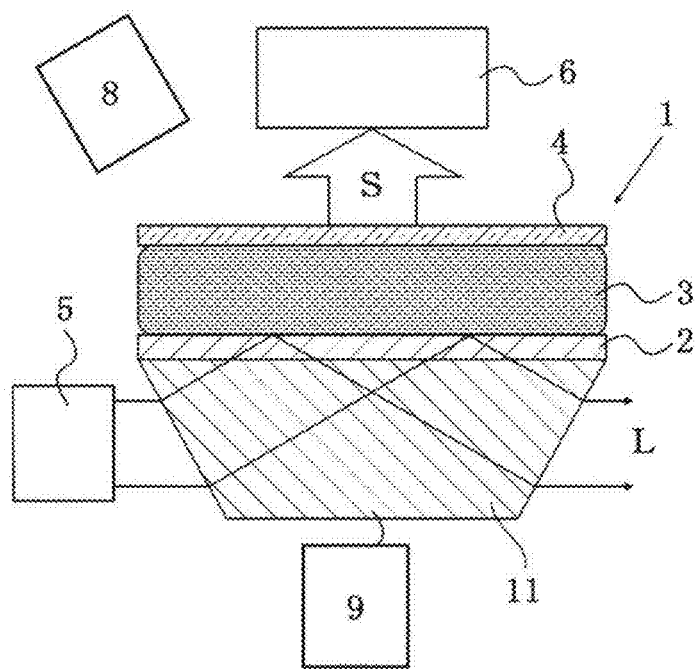
FIG. 2 is a schematic view of a modified example of the optical detection device comprising a magnetic-field applying means of one embodiment of the present invention.

FIG. 2 is a modified example of the optical detection device used in the embodiment of the present invention. The optical detection device 1 in FIG. 2 comprises a drawing magnetic field application unit 9 configured to draw the conjugates toward the surface of the sensing plate 2, and is similar to the configuration of FIG. 1 other than this. The optical detection device 1 firstly draws the conjugates close to the surface of the sensing plate 2 by applying a drawing magnetic field, and then applies a first magnetic field to the conjugates. Such a drawing magnetic field can draw many conjugates close to the surface of the sensing plate 2 in a short period of time. When the first magnetic field, such as an away magnetic field, is applied subsequently, a decrease in optical signal or the movement of the optical signal can be observed more, and so this device enables more sensitive detection of the target substance. This configuration is very effective when gravitational sedimentation of the conjugates is difficult, when the time required for the detection has to be shortened greatly, or when the sensing plate 2 is disposed above or lateral to the mixture solution 3.

First Embodiment

Figure 3:
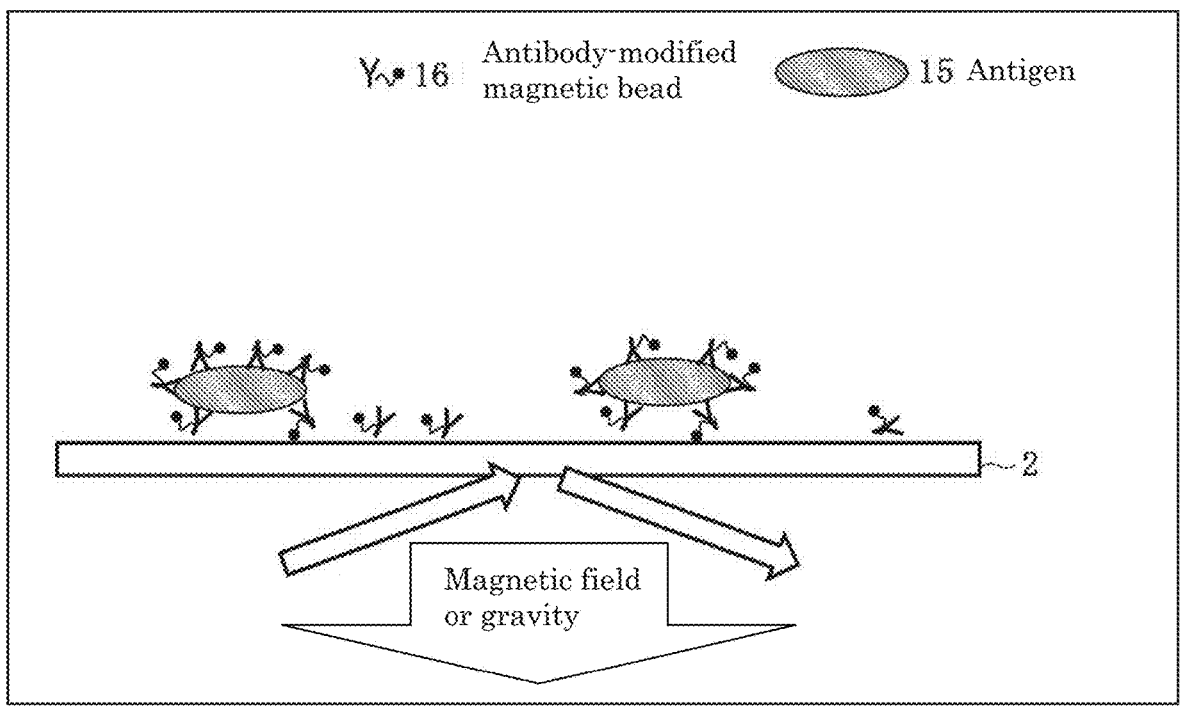
FIG. 3 explains the action during applying a drawing magnetic field or gravitational sedimentation in a first embodiment of the present invention.
Figure 4:
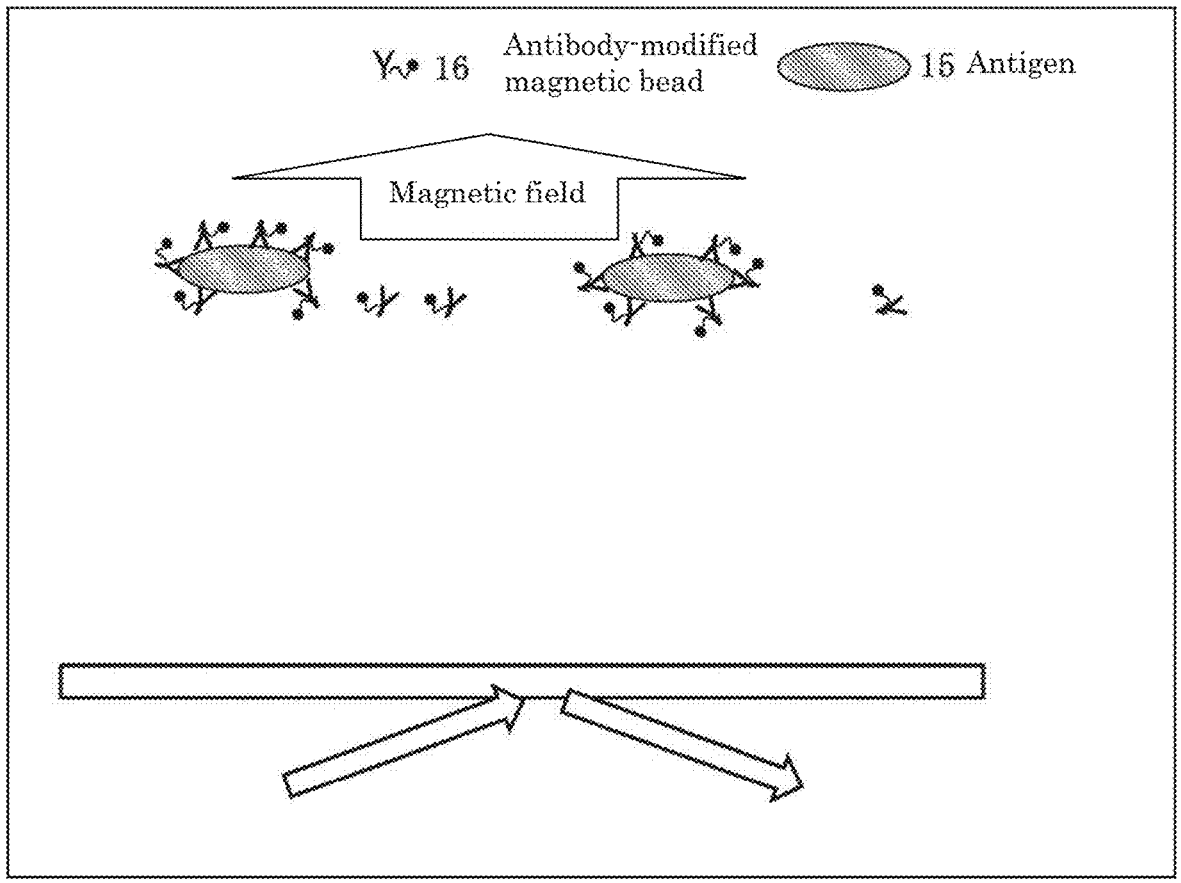
FIG. 4 explains the action during applying an away magnetic field in the first embodiment of the present invention.

Referring to FIGS. 3 and 4, the following describes the first embodiment of the present invention. This embodiment describes the case where the target substance itself emits an optical signal. One or more magnetic particles can bond with the target substance in the sample. FIGS. 3 and 4 show the case where a plurality of magnetic particles bond with one target substance to form a conjugate. In FIGS. 3 and 4, a near field not illustrated is formed by the light irradiated from the side of the rear face of the sensing plate 2 under the condition of total reflection and is generated on the surface of the sensing plate. The conjugates are detected by the device shown in FIG. 1 or FIG. 2. FIGS. 3 and 4 show a magnetic bead with antibody (hereinafter called antibody-modified magnetic bead) 16 as an example of the magnetic particle and show an antigen 15 as an example of the target substance.

FIG. 3 shows the state where one or both of the gravitational sedimentation and the drawing magnetic field acts to draw the conjugates toward the surface of the sensing plate 2. In this state, as shown in FIG. 3, the antibody-modified magnetic bead 16 as a single body that does not form a conjugate also is drawn to the surface of the sensing plate 2. FIG. 4 explains the state after the application of an away magnetic field. When the drawing magnetic field is applied in FIG. 3, the application of such a drawing magnetic field is stopped, and then the away magnetic field is applied. As shown in FIG. 4, the conjugates and antibody-modified magnetic beads 16 as single bodies move away from the surface of the sensing plate 2 due to the away magnetic field.

When a magnetic field for parallel movement is applied to the surface of the sensing plate 2, which is not illustrated, conjugates and antibody-modified magnetic beads 16 as single bodies can move in the vicinity of the surface of the sensing plate 2 and in parallel to the surface or can change the orientation due to the magnetic field for parallel movement.

In the state of FIG. 3, the antigens 15 in the near field on the surface of the sensing plate 2 generate optical signals. Next, an away magnetic field or a magnetic field for parallel movement is applied to the surface of the sensing plate 2, then the conjugates move away from the surface of the sensing plate 2, move in the vicinity of the surface, or change the orientation. As a result, optical signals from the antigens 15 attenuate, disappear or move. The antigens 15 can be detected by detecting such attenuation, disappearance or movement of the optical signal.

Such attenuation or disappearance of the optical signal can be observed by measuring the total amount of optical signal emitted from a certain region on the surface of the sensing plate 2, for example. In this case, a photodiode or a photomultiplier can be used for the photodetector, for example. A difference in the total amount of optical signal emitted from the certain region may be measured between the application of the away magnetic field or the magnetic field for parallel movement and after a certain period of time has elapsed since the application of such a magnetic field, or the total amount of optical signal may be acquired over time while applying the away magnetic field or the magnetic field for parallel movement to measure a change with the passage of time.

For another method for observing the attenuation, disappearance and movement of the optical signal, the optical signal may be observed two-dimensionally as an image, and the attenuation, disappearance and movement of the optical signal may be observed in the image. In this case, image sensors, such as a CCD image sensor and a CMOS image sensor, can be used for the photodetector. For instance, when optical signals observed at the point of emitting the optical signals attenuate, disappear or move due to the application of the away magnetic field or the magnetic field for parallel movement, the number of the points corresponding to such attenuation, disappearance or movement of the optical signals can be counted, whereby the target substance can be detected.

Second Embodiment

Figure 5:
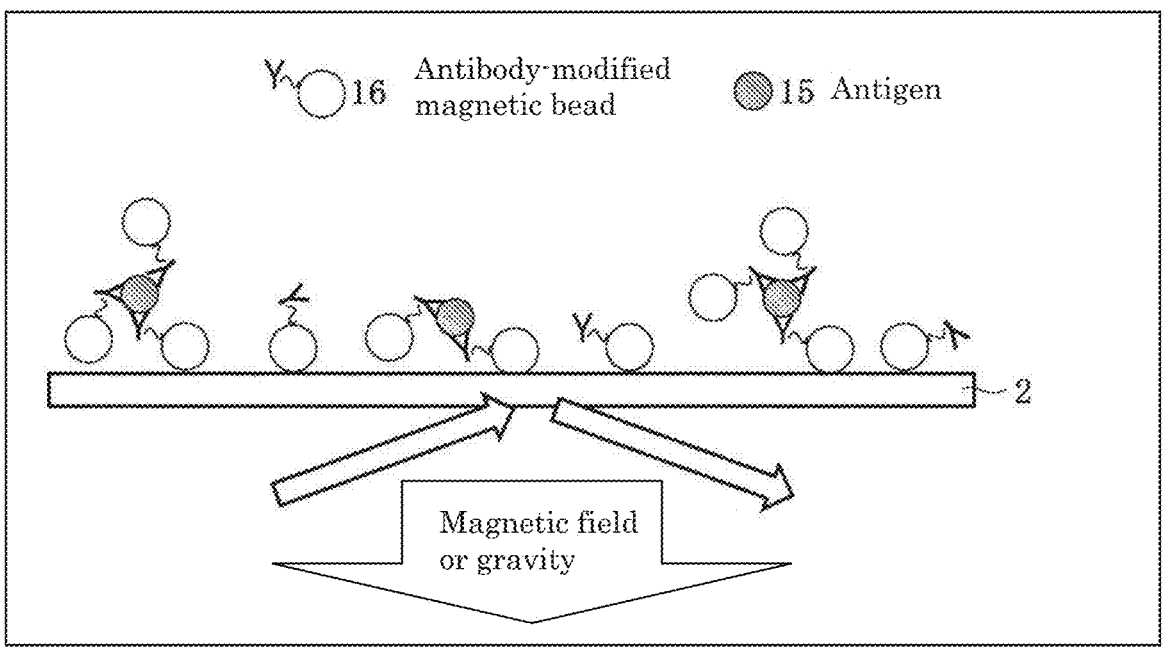
FIG. 5 explains the action during applying a drawing magnetic field or gravitational sedimentation in the second embodiment of the present invention.
Figure 6:
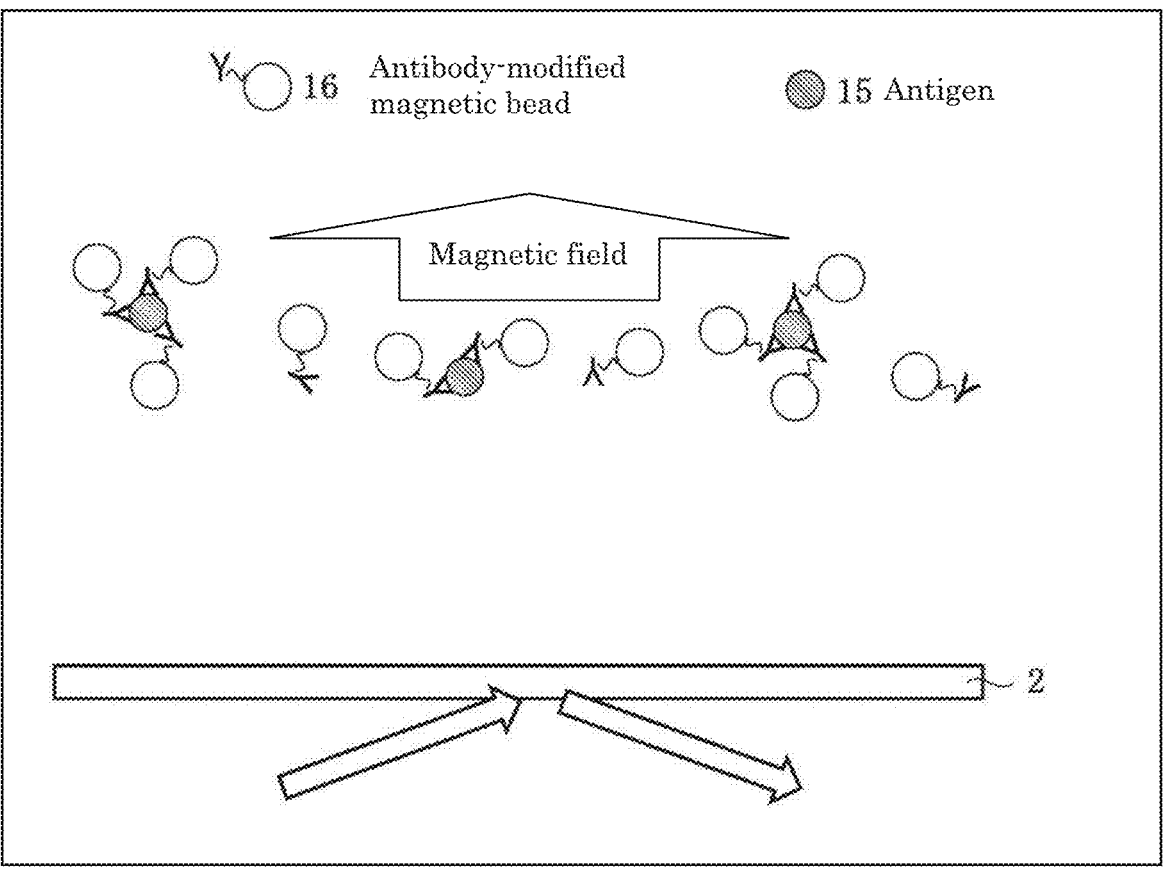
FIG. 6 explains the action during applying an away magnetic field in the second embodiment of the present invention.

Referring to FIGS. 5 and 6, the following describes the second embodiment of the present invention. The present embodiment is for a target substance that emits a weak optical signal or does not generate an optical signal, and detects an optical signal emitted from a magnetic particle to detect the target substance in the sample. In this case, the magnetic particle emits fluorescence or scattered light. Preferably two or more magnetic particles bond with a target substance to form a conjugate in the present embodiment.

FIGS. 5 and 6 show the case where two or more magnetic particles bond with one target substance to form a conjugate. In FIGS. 5 and 6, a near field not illustrated is formed by light irradiated from the side of the rear face of the sensing plate 2 under the condition of total reflection and is generated on the surface of the sensing plate. The conjugates are detected by the device shown in FIG. 1 or FIG. 2. FIGS. 5 and 6 show an antibody-modified magnetic bead 16 as an example of the magnetic particle and show an antigen 15 as an example of the target substance.

FIG. 5 shows the state where one or both of the gravitational sedimentation and the drawing magnetic field acts to draw the conjugates of the magnetic particles and the target substance toward the surface of the sensing plate 2. In this state, as shown in FIG. 5, the antibody-modified magnetic bead 16 as a single body that does not form a conjugate also is drawn to the surface of the sensing plate 2. FIG. 6 explains the state after the application of an away magnetic field. When the drawing magnetic field is applied in FIG. 5, the application of such a drawing magnetic field is stopped, and then the away magnetic field is applied. As shown in FIG. 6, the conjugates and antibody-modified magnetic beads 16 as single bodies move away from the surface of the sensing plate 2 due to the away magnetic field.

When a magnetic field for parallel movement is applied to the surface of the sensing plate 2, which is not illustrated, conjugates and antibody-modified magnetic beads 16 as single bodies can move in the vicinity of the surface of the sensing plate 2 and in parallel to the surface or can change the orientation due to the magnetic field for parallel movement.

In the state of FIG. 5, the conjugates and the antibody-modified magnetic beads 16 as single bodies in the near field on the surface of the sensing plate 2 emit optical signals. Next as shown in FIG. 6, when an away magnetic field or a magnetic field for parallel movement is applied to the surface of the sensing plate 2, the conjugates and the antibody-modified magnetic beads 16 as single bodies move away from the surface of the sensing plate 2 or move in the vicinity of the surface. As a result, optical signals from the conjugates and the antibody-modified magnetic beads 16 as single bodies attenuate, disappear or move. At this time, since each conjugate is bonded to two or more antibody-modified magnetic beads 16 bonded, such a conjugate can emit a larger optical signal than from the antibody-modified magnetic bead 16 as a single body. Optical signals in FIG. 5 may be observed two-dimensionally as an image, and the strength of the optical signals emitted from the antibody-modified magnetic beads 16 as single bodies may be measured. When there is a point of emitting an optical signal that is stronger than the optical signal from the antibody-modified magnetic beads 16 as single bodies, and the strength of such an optical signal attenuates, disappears or moves due to the application of the away magnetic field or the magnetic field for parallel movement, this corresponds to the movement of the conjugate away from the surface of the sensing plate 2 or the movement of the conjugate in the vicinity of the surface due to the application of the away magnetic field or the magnetic field for parallel movement. Such attenuation, disappearance or movement of the optical signal may be detected, whereby the antigen 15 can be detected.

The second embodiment cannot use the method detecting the target substance by observing the total amount of optical signals generated from a certain region on the surface of the sensing plate 2 as in the first embodiment. This is because in the second embodiment the total amount of optical signals that attenuate or disappear due to the application of an away magnetic field or a magnetic field for parallel movement in a certain region on the surface of the sensing plate 2 depends on the total amount of the antibody-modified magnetic beads 16, and does not depend on the presence or not of the antigens 15 or the amount of the antigens 15.

Third Embodiment

Figure 7:
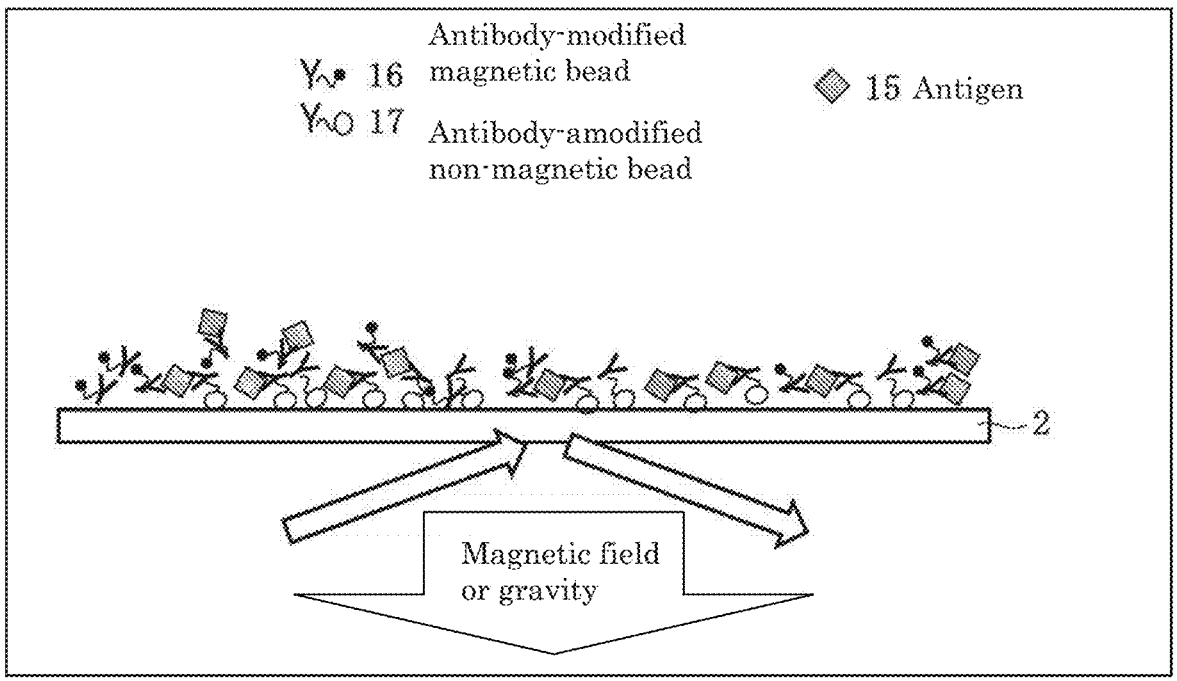
FIG. 7 explains the action during applying a drawing magnetic field or gravitational sedimentation in the third embodiment of the present invention.
Figure 8:
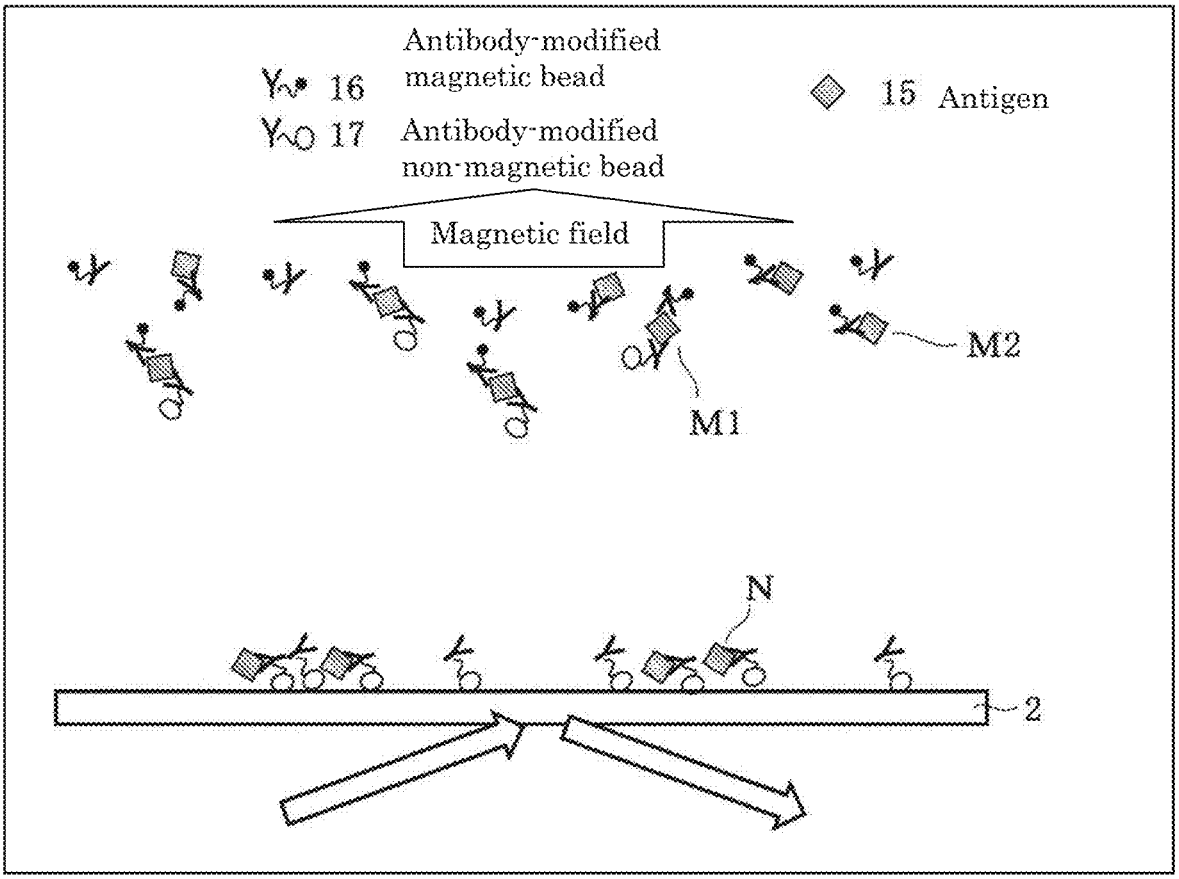
FIG. 8 explains the action during applying an away magnetic field in the third embodiment of the present invention.

Referring to FIGS. 7 and 8, the following describes the third embodiment of the present invention. This embodiment describes the case where a magnetic particle and a labeled substance bond with a target substance in a sample. Although this embodiment explains the case where the labeled substance is dye so that the target substance itself has a function of emitting a fluorescent signal, the following describes another case of a target substance sandwiched between a magnetic particle and a labeled substance, i.e., a sandwich structure, as an example.

FIGS. 7 and 8 show the case where one magnetic particle and one labeled substance bond with one target substance to form a conjugate. A plurality of magnetic particles and a plurality of labeled substances may bond with a target substance to form a conjugate. In FIGS. 7 and 8, a near field not illustrated is formed by light irradiated from the side of the rear face of the sensing plate 2 under the condition of total reflection and is generated on the surface of the sensing plate 2. The conjugates are detected by the device shown in FIG. 1 or FIG. 2. FIGS. 7 and 8 show an antibody-modified magnetic bead 16 as an example of the magnetic particle, an antibody-modified labeled substance (this may be called an "antibody-modified non-magnetic bead 17") as an example of the labeled substance, and an antigen 15 as an example of the target substance. When the antigens 15, the antibody-modified magnetic beads 16 and the antibody-modified non-magnetic beads 17 are mixed, a plurality of types of conjugates may be generated as follows. That is, a conjugate M1 of an antigen 15, an antibody-modified magnetic bead 16 and an antibody-modified non-magnetic bead 17, a conjugate M2 of an antigen 15 and an antibody-modified magnetic bead 16 (an antibody-modified non-magnetic bead 17 does not bond), a conjugate N of an antigen 15 and an antibody-modified non-magnetic bead 17 (an antibody-modified magnetic bead 16 does not bond), an antibody-modified magnetic bead 16 as a single body that does not form a conjugate, and an antibody-modified non-magnetic bead 17 as a single body that does not form a conjugate may be present in the sample.

FIG. 7 shows the state where one or both of the gravitational sedimentation and the drawing magnetic field acts to draw the conjugates M1 toward the surface of the sensing plate 2. In this state, as shown in FIG. 7, the conjugates M2 and the antibody-modified magnetic beads 16 as single bodies also are drawn to the surface of the sensing plate 2. The conjugates N and the antibody-modified non-magnetic beads 17 as single bodies also may be present in the vicinity of the surface of the sensing plate 2 due to gravitational sedimentation or non-specific adsorption to the surface of the sensing plate 2. FIG. 8 explains the state after the application of an away magnetic field. When the drawing magnetic field is applied in FIG. 7, the application of such a drawing magnetic field is stopped, and then the away magnetic field is applied. As shown in FIG. 8, the conjugates M1, the conjugates M2 and the antibody-modified magnetic beads 16 as single bodies move away from the surface of the sensing plate 2 due to the away magnetic field. On the contrary, the conjugates N and the antibody-modified non-magnetic beads 17 as single bodies remain in the vicinity of the surface of the sensing plate 2 and do not move.

When a magnetic field for parallel movement is applied to the surface of the sensing plate 2, which is not illustrated, the conjugates M1, the conjugates M2 and the antibody-modified magnetic beads 16 as single bodies can move in the vicinity of the surface of the sensing plate 2 and in parallel to the surface or can change the orientation due to the magnetic field for parallel movement.

In the state of FIG. 7, the antibody-modified non-magnetic beads 17 in the near field on the surface of the sensing plate 2 emit optical signals. Next when an away magnetic field or a magnetic field for parallel movement is applied to the surface of the sensing plate 2 as shown in FIG. 8, the conjugates M1 move away from the surface of the sensing plate 2 or move in the vicinity of the surface of the sensing plate 2. As a result, optical signals from the antibody-modified non-magnetic beads 17 that bond with the conjugates M1 attenuate, disappear or move. Therefore the antigens 15 can be detected by detecting such attenuation, disappearance or movement of the optical signals. At this time, the antigens 15 that bond with the conjugate M2 and the conjugate N are not detected. Note here that an antibody that bonds with the antigen 15 well may be used as the antibody of the antibody-modified magnetic beads 16 and the antibody-modified non-magnetic beads 17, whereby the number of the conjugates M2 and the conjugates N can be decreased and the number of the conjugates M1 can be increased, and so more antigens 15 can be detected.

Such attenuation or disappearance of signals may be observed by a method similar to that described in the first embodiment.

In the first, second and third embodiments, when the drawing magnetic field is applied, the application of such a drawing magnetic field is stopped, and then an away magnetic field or a magnetic field for parallel movement is applied. Instead, if an away magnetic field and a magnetic field for parallel movement can move a conjugate of a target substance bonding with a magnetic particle away from the surface of the sensing plate 2 or move the conjugate while keeping the application of a drawing magnetic field, the application of such a drawing magnetic field can be kept. For instance, this can be realized by making the away magnetic field or the magnetic field for parallel movement much stronger than the drawing magnetic field.

(About Near Field)

Figure 9:
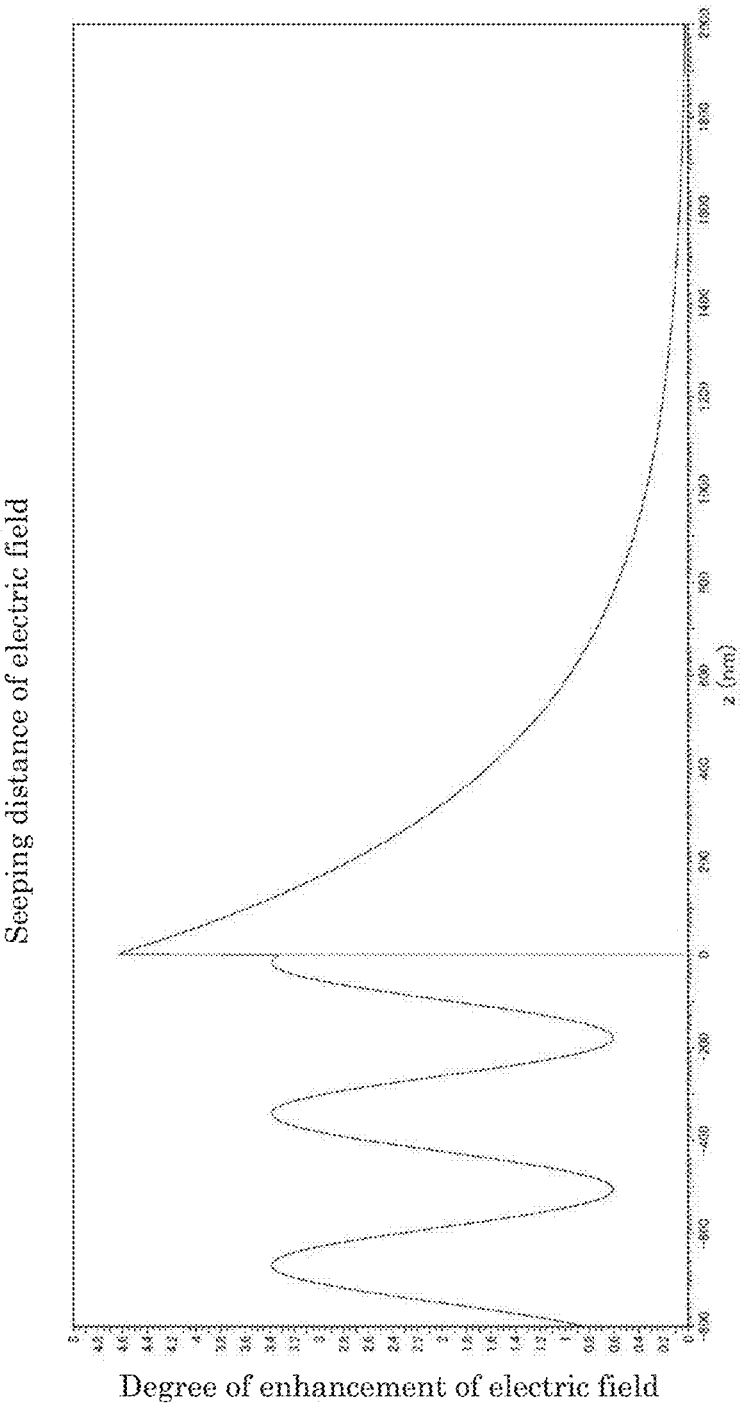
FIG. 9 shows the relationship between the distance from the surface of the sensing plate and the intensity of the enhanced electric field in the optical detection device of the present invention.

The following describes a specific example of the near field that is required in the first to third embodiments, by way of an example of $SiO_2$ substrate as the sensing plate. FIG. 9 shows the result of calculated distribution of the strength of the electric field that is an evanescent field obtained from $SiO_2$ glass as the sensing plate, on the surface of which water is placed, and on the rear face of which a prism made of $SiO_2$ glass is in optically close contact, and monochromatic light as p polarization of 375 nm falls on the surface at the incident angle of 67°. The horizontal axis z indicates the distance (nm) from the surface of the sensing plate, and z=0 indicates the surface of the sensing plate. As is known from FIG. 9, letting that the incident light has the strength of 1, the electric field on the surface of the sensing plate has the strength of about 4.5. The strength of the electric field as the evanescent field decreases with distance from the surface of the sensing plate, and reaches substantially 0 when the distance from the surface of the sensing plate is 2000 nm. When conjugates move away from the surface of the sensing plate by applying an away magnetic field, the strength of the electric field as in FIG. 9 attenuates or disappears, so that optical signals attenuate or disappear.

(Verification of Measurement Principle)

The following shows an example of the experiment to verify the measurement principle of one embodiment of the present invention. Considering scattered light from magnetic particles themselves as optical signals, the experiment observed disappearance of the optical signals as the magnetic particles moved away from the surface of the sensing plate. In this experiment, the device of FIG. 1 was used. For the sensing plate 2, a $SiO_2$ substrate of 0.75 mm in thickness was used. For the light source 5, a white LED light source (produced by Thorlabs Inc., model number: MWWHF2) was used. A prism 11 made of $SiO_2$ glass was brought in optically close contact with the rear face of the sensing plate 2, and white light from the light source 5 was allowed to fall on the surface of the sensing plate 2 at the incident angle of 67°. The magnetic particles were magnetic beads of 1 μm in diameter. The density of the magnetic particles was 5 μg/ml. After dropping 10 μl of a liquid sample containing the magnetic particles on the $SiO_2$ substrate, it was left to stand for 5 minutes so that the magnetic particles settled out by gravitational sedimentation on the surface of the sensing plate 2. A near field was formed on the surface of the sensing plate 2 by the irradiation of the white light, and optical signals were measured. The optical signals were observed with an optical microscope equipped with a 10-power objective lens and a cooled CMOS camera (produced by BITRAN CORPORATION, model number: CS-51M). That is, as the light detection unit 6, the CMOS camera equipped with a 10-power objective lens was used. Before applying an away magnetic field, optical signals due to scattered light from the magnetic particles settled out by gravitational sedimentation and noise signals due to contaminants were observed in the near field at the same time, so that the magnetic particles were not distinguished from the contaminants at this time. Next, an away magnetic field was applied using a permanent magnet as an away magnetic field application unit that was one example of the first magnetic field application unit 8 to move the magnetic particles away from the surface of the sensing plate 2. Then, some of the light points that were observed with the CMOS camera before the application of magnetic field disappeared. In this way, the away magnetic field applied moved some of the magnetic particles away from the surface of the sensing plate, and as a result optical signals disappeared. This enabled distinguishing of the magnetic particles from the contaminants for detection.

Fourth Embodiment

Figure 10:
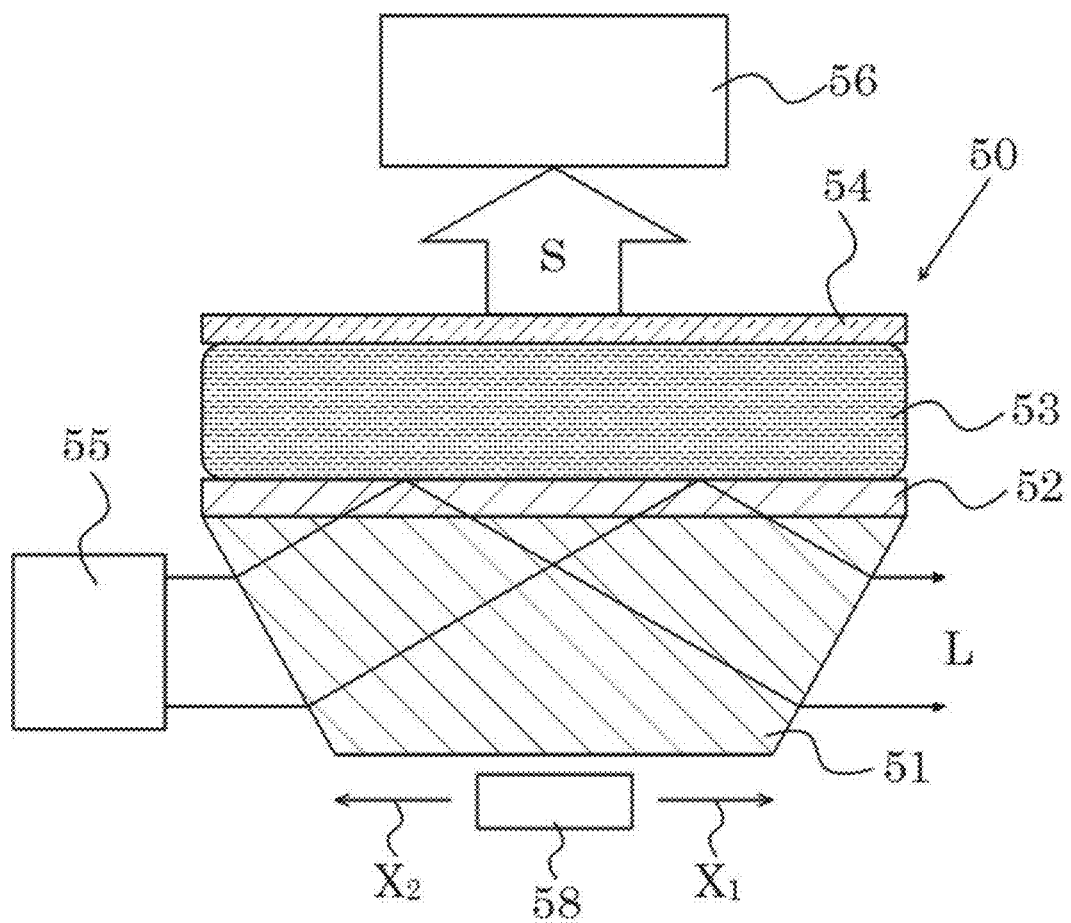
FIG. 10 describes the optical detection device according to the fourth embodiment.

Next the following describes an optical detection device according to the fourth embodiment of the present invention, with reference to FIG. 10. FIG. 10 describes the optical detection device according to the fourth embodiment.

As shown in FIG. 10, an optical detection device 50 according to the fourth embodiment is configured like a well-known surface plasmon resonance sensor, and comprises a prism 51, a sensing plate 52, a cover glass 54, a light source 55, a light detection unit 56, and a second magnetic field application unit 58. Reference numeral 53 in the drawing denotes the mixture solution of a sample containing a target substance, a magnetic particle, a labeled substance, and a weight substance (the labeled substance and the weight substance may not be included).

These prism 51, sensing plate 52, cover glass 54, light source 55 and light detection unit 56 can have a configuration similar to that of the prism 11, the sensing plate 2, the cover glass 4, the light source 5 and the light detection unit 6 in the optical detection device 1 described referring to FIG. 1. The optical detection device 50 according to the fourth embodiment is different from the optical detection device 1 in that the second magnetic field application unit 58 is arranged instead of the first magnetic field application unit 8. The following describes a difference.

The second magnetic field application unit 58 is disposed on the side of the rear face of the sensing plate 52, and can draw the conjugates in the mixture solution 53 that is introduced on the surface of the sensing plate 52 toward the surface of the sensing plate 52 by applying a magnetic field, and can move in the direction having a vector component parallel to the in-plane direction of the surface of the sensing plate 52 while applying the magnetic field. The second magnetic field application unit 58 comprises a permanent magnet and a sliding member (not illustrated) that slides the permanent magnet in $X_1$ direction or in $X_2$ direction.

The movement of the conjugate is carried out by a conjugate moving step, wherein when the second magnetic field application unit 58 as the magnetic field application unit applies the magnetic field to draw the conjugates in the mixture solution 53 introduced on the surface of the sensing plate 52 toward the surface of the sensing plate 52, and the second magnetic field application unit 58 moves in the direction having a vector component parallel to the in-plane direction of the surface of the sensing plate 52, then the conjugates move with the movement of the second magnetic field application unit 58 or change the orientation (the conjugate moving step). When the second magnetic field application unit 58 is configured with a plurality of members that are disposed in an annular shape, the conjugate moving step may be performed by controlling the magnetic field applied to each of the members and without using the sliding member.

When the second magnetic field application unit 58 is used, because of drawing all or a part of the conjugates in the mixture solution 53 on the surface of the sensing plate 52 by applying a magnetic field, it is possible to omit the time of waiting for the gravitational sedimentation that allows the conjugates floating in the liquid layer of the mixture solution 53 to settle out on the surface of the sensing plate 52 after introducing the mixture solution 53 on the surface of the sensing plate 52.

Figure 11:
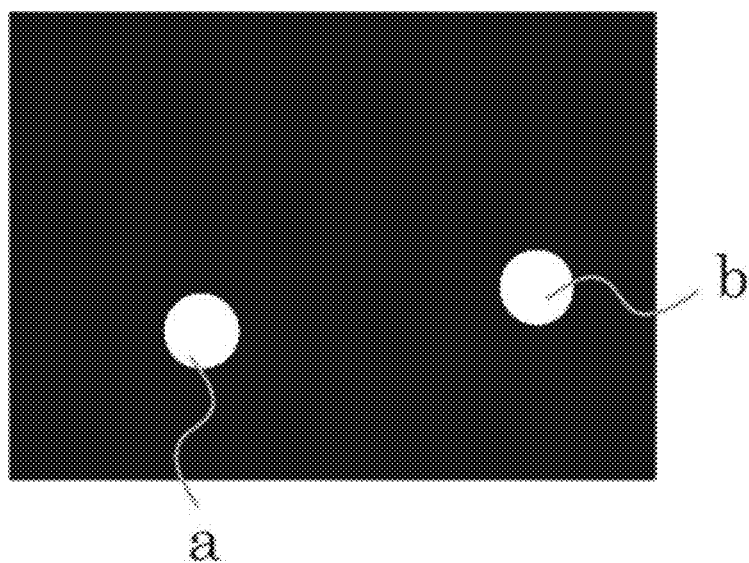
FIG. 11 is drawing (1) showing the state on the surface of the sensing plate 52 before the conjugate moving step.
Figure 12:
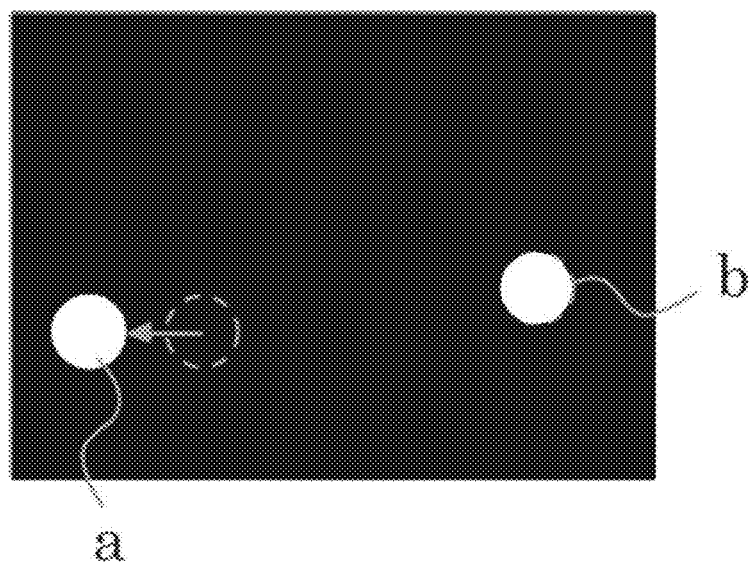
FIG. 12 is drawing (1) showing the state on the surface of the sensing plate 52 after the conjugate moving step.

The optical detection device 50 thus configured can obtain optical signals (two-dimensional image) before and after the conjugate moving step as shown in FIGS. 11 and 12, and this can clearly distinguish an optical signal a of the target substance from noise signal b due to scratches on the surface of the sensing plate 52, contaminates adsorbed to or present on the surface, fluctuation of the output from the light source and the like. FIG. 11 shows the state on the surface of the sensing plate 52 before the conjugate moving step, and FIG. 12 shows the state on the surface of the sensing plate 52 after the conjugate moving step.

Figure 13:
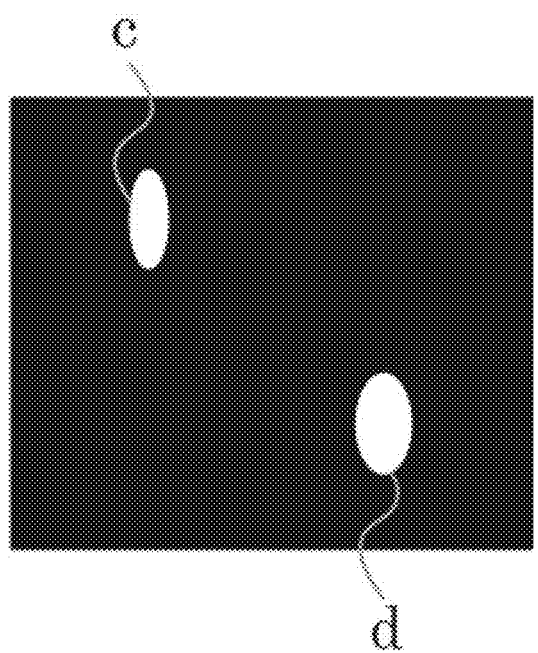
FIG. 13 is drawing (2) showing the state on the surface of the sensing plate 52 before the conjugate moving step.
Figure 14:
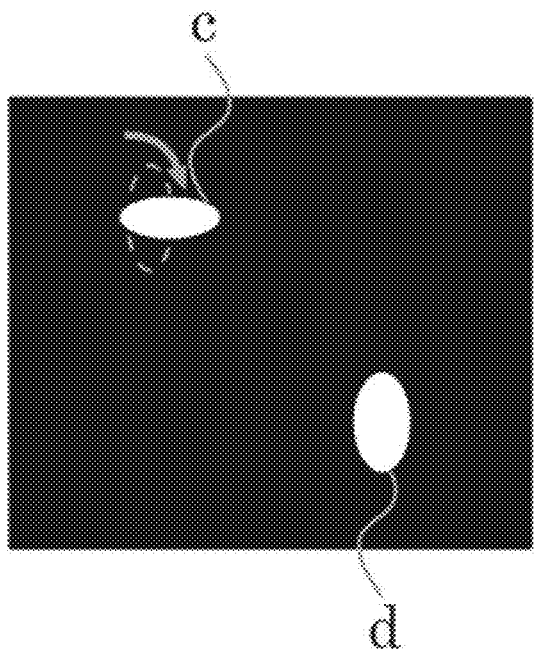
FIG. 14 is drawing (2) showing the state on the surface of the sensing plate 52 after the conjugate moving step.

When anisotropy can be observed for the shape of an optical signal (shape of the conjugate), the optical signal (two-dimensional image) before and after the conjugate moving step can be obtained as shown in FIGS. 13 and 14, and this can clearly distinguish an optical signal c of the target substance from noise signal d due to scratches on the surface of the sensing plate 52, contaminates adsorbed to or present on the surface, fluctuation of the output from the light source and the like. FIG. 13 shows the state on the surface of the sensing plate 52 before the conjugate moving step, and FIG. 14 shows the state on the surface of the sensing plate 52 after the conjugate moving step.

In this way, before and after the conjugate moving step, the conjugates move and the optical signals accordingly move. In addition, the orientation of the conjugates may change, and the optical signals accordingly change. Based on this, the optical detection device 50 can clearly distinguish a signal of the target substance from the noise signal for detection.

The optical detection device 1 of FIG. 1 is described above by way of the illustrated example of applying a magnetic field from the first magnetic field application unit 8 so as to move the conjugates away from the sensing plate 2 (see the first to third embodiments). Alternatively the first magnetic field application unit 8 may apply a magnetic field so as to move the conjugates in the direction having a vector component parallel to the in-plane direction of the surface of the sensing plate 2. In this case, the optical detection device can detect the target substance based on the movement of the optical signals in the direction having a vector component parallel to the in-plane direction of the surface of the sensing plate 2 along with the movement of the conjugates similarly to the optical detection device 50.

Also when anisotropy of the shape of the optical signals (the shape of the conjugate) can be detected, the optical detection device 1 can detect the target substance based on a change in the optical signals due to such a change in orientation of the conjugates similarly to the optical detection device 50.

Example 1

The following describes examples. In this example, the optical detection device 1 of FIG. 1 was used. For the sensing plate 2, a $SiO_2$ substrate of 0.75 mm in thickness was used. For the light source 5, a white LED light source (produced by Thorlabs Inc., model number: MWWHF2) was used, and an optical fiber having a collimator lens at the emitting end and having the core diameter of 600 μm was used. A prism 11 made of $SiO_2$ glass was arranged in optically close contact with the rear face of the sensing plate 2, and white light from the light source 5 was incident on the prism 11 via a polarization filter on the surface of the sensing plate 2 at the incident angle of 67° so that S-polarized light was incident on the sensing plate 2.

In this example, the detection method described in the third embodiment was used. For the target substance, normal mouse IgG was selected. For the magnetic particles, particles including magnetic labeled beads of 25 nm in diameter bonding with antimouse IgG-donkey antibody were used. For the labeled substance, particles including polystyrene beads of 500 nm in diameter bonding with antimouse IgG-rabbit antibody were used. These magnetic particles and labeled substance were mixed in the solution containing the target substance to prepare a mixture solution, and then 10 µl of this mixture solution was introduced into the liquid holding part on the sensing plate 2. This mixture solution was left to stand for 10 minutes so that the magnetic particles settled out by gravitational sedimentation on the surface of the sensing plate 2. The mixture solution in this state was irradiated with the white light so that a near field was formed on the surface of the sensing plate 2, and optical signals were measured. The optical signals were observed with an optical microscope equipped with a 10-power objective lens and a cooled CMOS camera (produced by BITRAN CORPORATION, model number: CS-51M). That is, as the light detection unit 6, the CMOS camera equipped with a 10-power objective lens was used.

Figure 15A:
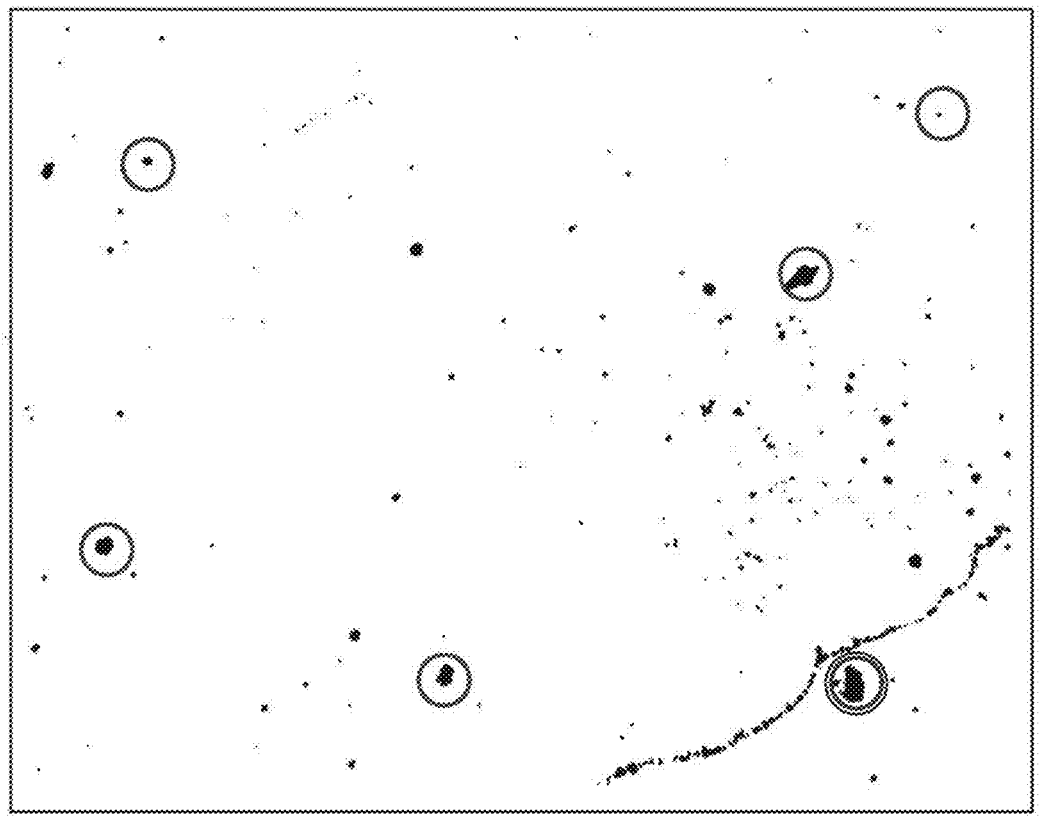
FIG. 15A explains the state before the application of an away magnetic field in Example 1 of the present invention.
Figure 15B:
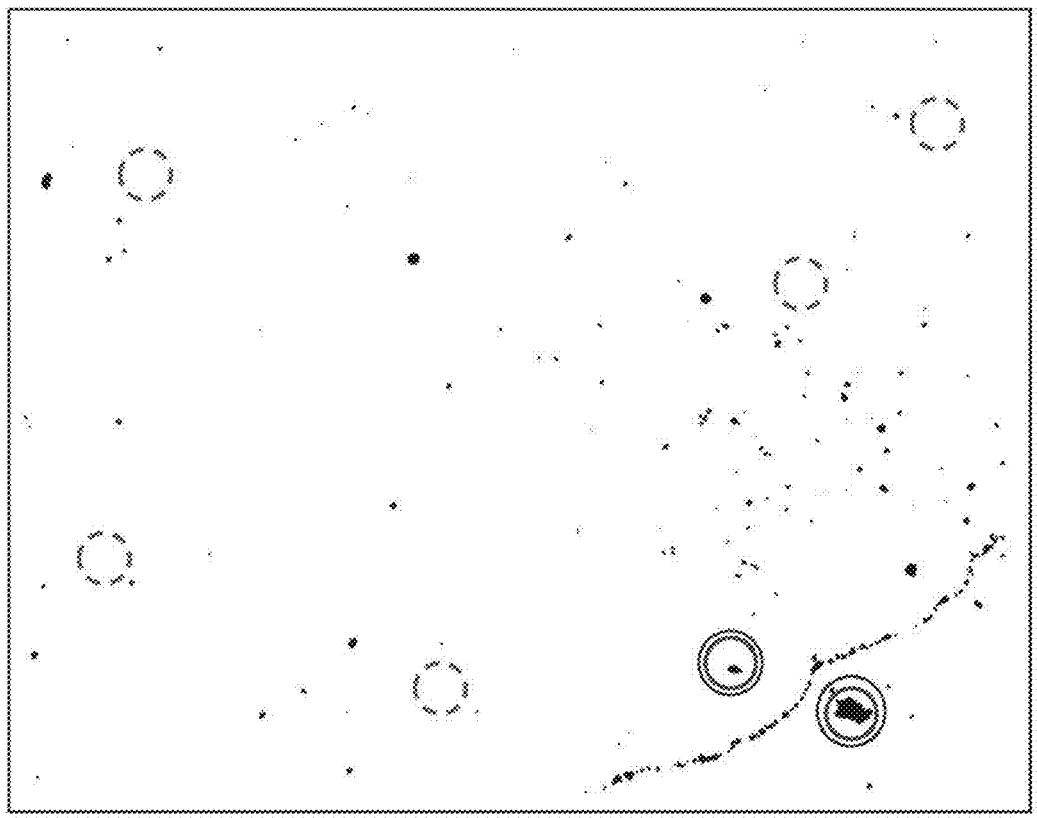
FIG. 15B explains the state after the application of the away magnetic field in Example 1 of the present invention.

FIG. 15A shows an observed image. FIG. 15A shows an image subjected to white/black inversion so that the background was white and the position for optical signals detected was black as well as binarization. The image has the field of view of about 300 µm×225 µm. In this drawing, a few tens to about one hundred of individual light spots were confirmed as black points that were spread through the entire field of view. FIG. 15B shows an image observed after an away magnetic field was applied using a permanent magnet as the first magnetic field application unit 8. This drawing shows the image subjected to the image processing similar to FIG. 15A. The image has the same field of view as in FIG. 15A. Solid circles, dashed-line circles and double circles in FIGS. 15A and 15B are added for illustrative purposes. When the away magnetic field was applied to move the magnetic particles away from the surface of the sensing plate 2, then at least five points (present in the area surrounded with the solid circles in the drawing) of the light spots in FIG. 15A, which were observed with the CMOS camera before the application of the magnetic field, disappeared in FIG. 15B (not present in the area surrounded with dashed-line circles in the drawing). At least two points (present in the area surrounded with the double circles in FIGS. 15A and 15B) moved to the area where their light spots were observable after the application of the magnetic field as well. The disappearing or moving light spots results from the movement of conjugates of the target substance, the magnetic particle and the labeled substance away from the surface of the sensing plate 2 due to the away magnetic field, or just the movement. In this example, observation after the application of magnetic field was conducted after the application of the away magnetic field stopped. That is, the conjugates moved away from the surface of the sensing plate 2 were then brought close to the surface of the sensing plate again due to gravitational sedimentation for observation. Presumably the movement of the conjugates, which was shown in this example, was observed in this way.

In this way, a difference in optical signals between before and after the application of the magnetic field enables the detection of the conjugates only, whereby the target substance can be detected while suppressing erroneous detection.

Example 2

Based on the configuration of the optical detection device 1 as shown in FIG. 1, an optical detection device according to Example 2 was prepared as follows. A sensing plate 2 in Example 2 was configured with a $SiO_2$ layer of 0.75 mm in thickness as a light-transmissive substrate, on which a Si layer of 36 nm in thickness and a $SiO_2$ layer of 365 nm in thickness were stacked in this order. Then, a self-assembled monolayer made of methoxy oligoethylene glycol-silane compound was formed on the surface of the sensing plate 2 for surface treatment to suppress adsorption of conjugates and contaminants.

For the light source 5, a wavelength-variable light source (SM-10YN, produced by Bunkoukeiki Co., Ltd) having the wavelength accuracy of ±1 nm, the half width of 10 nm, and the irradiation wavelength range of 300 to 1100 nm was used. An optical fiber having a collimator lens at the emitting end and having the core diameter of 600 µm was used to introduce monochromatic light of 644 nm in wavelength to the prism 11 via a polarization filter so that S-polarized light was incident on the sensing plate 2. The incident angle of the light irradiated from the rear face of the sensing plate 2 was inclined relative to the thickness direction of the sensing plate by 67.6°. Irradiation with the light under this condition excited a waveguide mode in the $SiO_2$ layer of the sensing plate 2, so that an enhanced electric field was formed on the surface of the sensing plate 2. Note here that the critical angle that is the minimum angle for the total-reflection condition of this optical system and is represented as the inclination angle relative to the thickness direction of the sensing plate 2 is 66.1°. For the light detection unit 6, the CMOS camera equipped with a 10-power objective lens was used similarly to Example 1.

A detection test of a target substance was conducted as follows using the optical detection device of Example 2. In this example, the detection method described in the third embodiment was used. Firstly antimouse IgG-donkey antibody-modified magnetic labeled beads (magnetic particles) of 25 nm in diameter, antimouse IgG-rabbit antibody-modified polystyrene beads (labeled substance) of 500 nm in diameter, and normal mouse IgG (target substance), which were similar to those used in Example 1, were mixed to prepare a mixture solution, which was left to stand for 30 minutes after the mixing. Then, 10 µl of the mixture solution was introduced into the liquid holding part on the surface of the sensing plate 2. Next, the rear face of the sensing plate 2 was irradiated with the monochromatic light with the wavelength of 644 nm from the light source 5. Next while the detection region on the surface of the sensing plate 2 was observed with the light detection unit 6 in the form of a two-dimensional image by setting the exposure time at 100 ms, the magnetic field was applied thereto by bringing the permanent magnet as the first magnetic field application unit 8 close to the surface of the sensing plate 2.

Figure 16A:
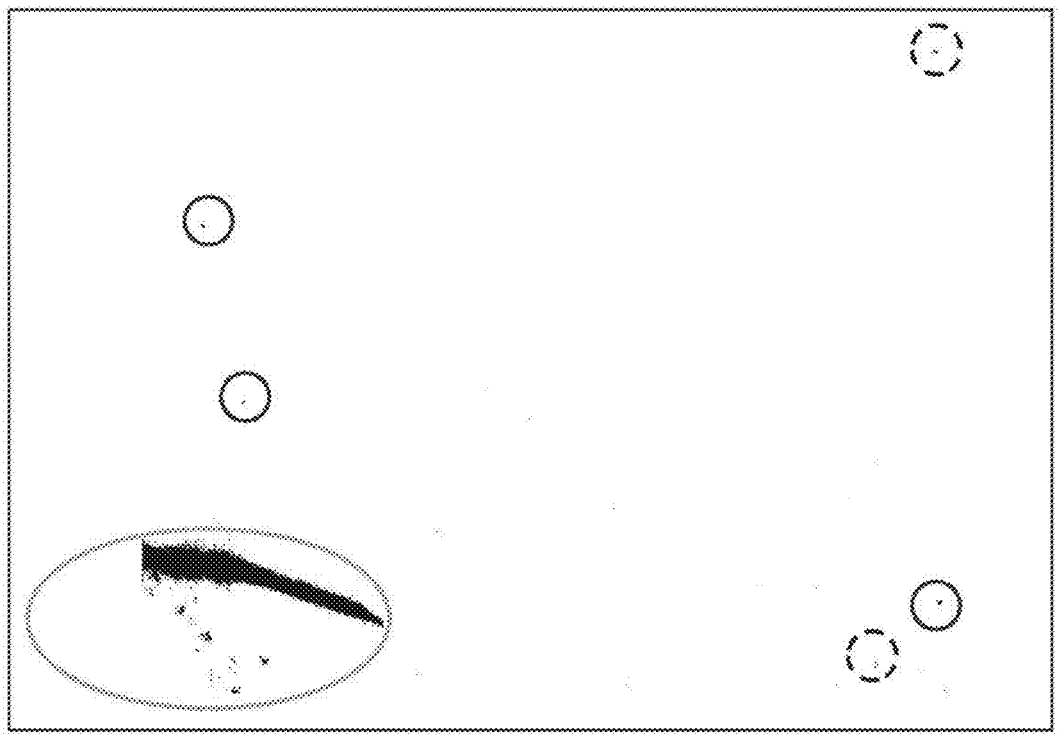
FIG. 16A explains a change during the application of the away magnetic field in Example 2 of the present invention.
Figure 16B:
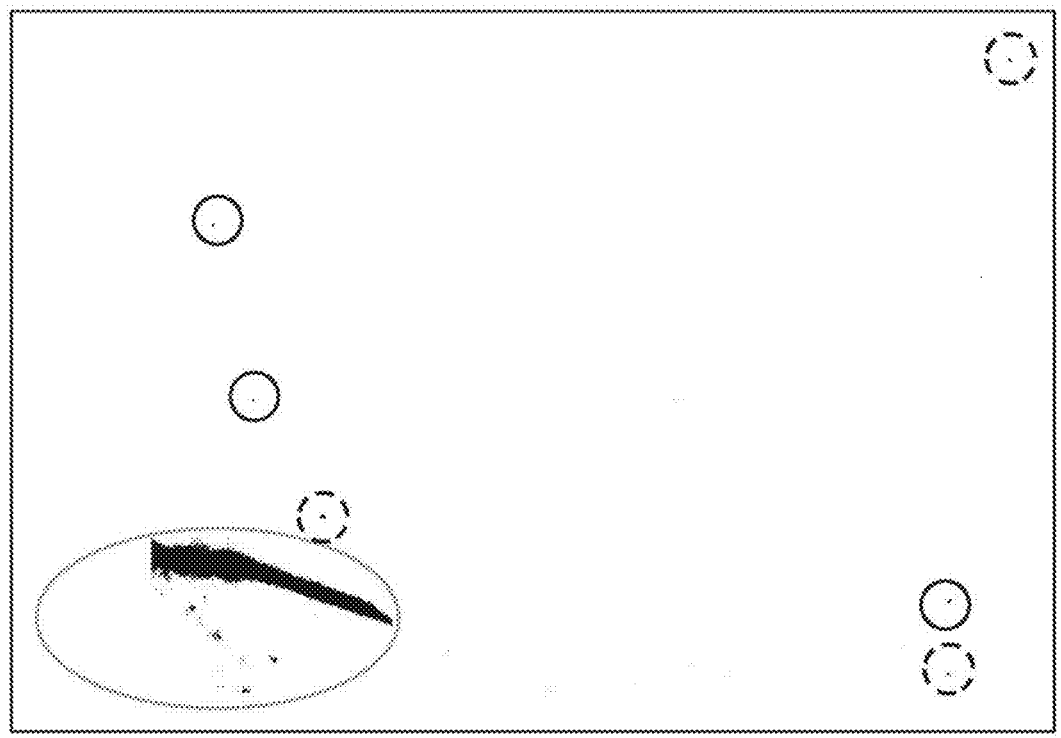
FIG. 16B explains a change during the application of the away magnetic field in Example 2 of the present invention.
Figure 16C:
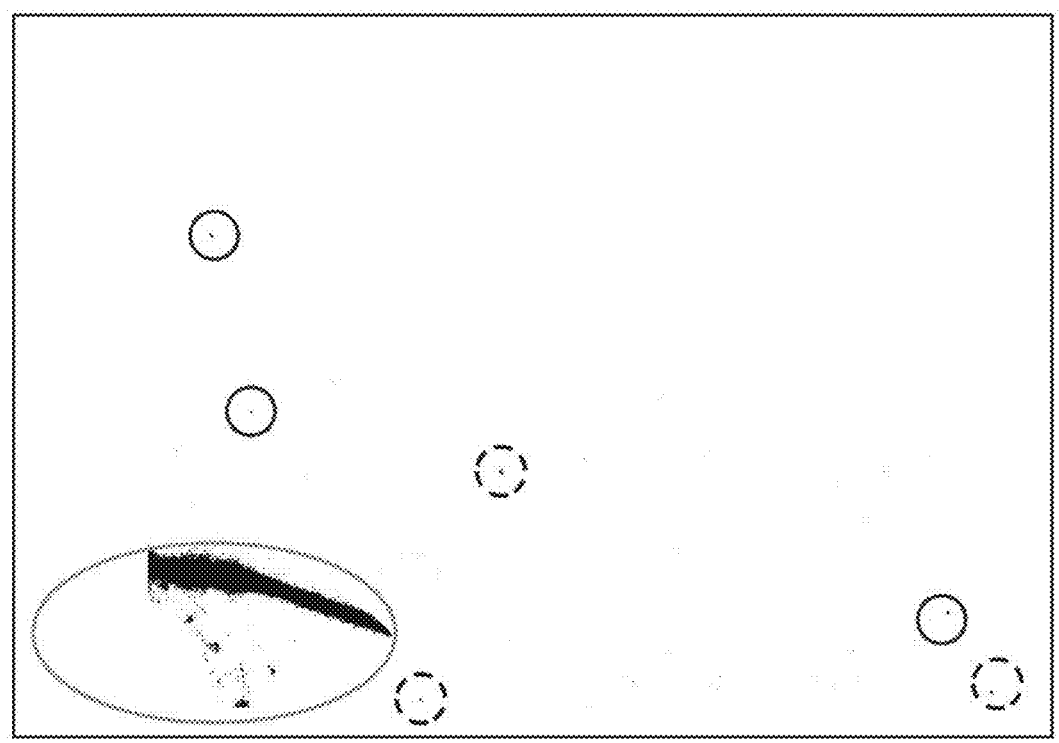
FIG. 16C explains a change during the application of the away magnetic field in Example 2 of the present invention.

FIGS. 16A, 16B and 16C show two-dimensional images that were obtained every second from the starting time of the observation in this example. FIGS. 16A, 16B and 16C show images subjected to white/black inversion so that the background was white and the position for optical signals detected was black as well as binarization. The image has the field of view of about 450 µm×360 µm. Solid circles, dashed-line circles and ellipses in these drawings are added for illustrative purposes. In FIGS. 16A, 16B and 16C, scattered light due to a large bubble was observed at the lower left of the screen (in the area surrounded with ellipses in the drawings). Since two-dimensional image information was acquired, a signal from this area can be distinguished from a signal from the target substance during detection. In FIGS. 16A, 16B, and 16C, several individual light spots are observed as black points that are spread through the entire field of view, and they result from scattered light emitted from the polystyrene beads of 500 nm in diameter. When the conjugate of the antimouse IgG-donkey antibody-modified magnetic labeled beads of 25 nm in diameter, the antimouse IgG-rabbit antibody-modified polystyrene beads of 500 nm in diameter, and the normal mouse IgG as stated above (hereinafter called a "conjugate A", this corresponds to the conjugate M1 in the third embodiment) moves due to the magnetic field applied, it is observed in the form of the light spot that disappears or moves.

In FIGS. 16A to 16C, three light spots (present in the area surrounded with solid circles in the drawings) were not affected from the magnetic field applied, and therefore they were antimouse IgG-rabbit antibody-modified polystyrene beads of 500 nm in diameter that did not form the conjugate A. Unlike Example 1, surface modification with methoxy oligoethylene glycol-silane compound allowed most of the light spots of the polystyrene beads of 500 nm in diameter to move in the field of view due to the magnetic field applied. This shows that the surface modification had the effect of suppressing non-specific adsorption to the surface of the sensing plate and so suppressing noise.

In FIGS. 16A, 16B and 16C, two to three light spots in the drawings (present in the area surrounded with dashed-line circles in the drawings) disappeared or moved, which shows that they were antimouse IgG-rabbit antibody-modified polystyrene beads of 500 nm in diameter that formed the conjugates A. In this way, disappearance or movement of optical signals over time during the application of magnetic field was observed, whereby the conjugates A were detected successfully. In this way, the target substance can be detected while suppressing erroneous detection.

The above examples in the embodiments are described for easy understanding of the invention, and the present invention is not limited to the embodiments.

INDUSTRIAL APPLICABILITY

The optical detection device and method of the present invention can be widely applied to detect and determine the amount of a micro substance, including biologically relevant substances, such as DNA, RNA, proteins, viruses, and bacterium, and so are industrially effective.

REFERENCE SIGNS LIST 1, 50 optical detection device
2, 52 sensing plate
3, 53 mixture solution
4, 54 cover glass
5, 55 light source
6, 56 light detection unit
8 first magnetic field application unit
9 drawing magnetic field application unit
11, 51 prism
58 second magnetic field application unit
S optical signal
L light
M1 conjugate of a target substance, a magnetic particle and a (non-magnetic) labeled substance
M2 conjugate of a target substance and a magnetic particle
N conjugate of a target substance and a (non-magnetic) labeled substance

The invention claimed is:

1. An optical detection method for a target substance that detects fluorescence or scattered light as an optical signal from a conjugate comprising the target substance on a surface of a sensing plate in a near field,
the optical detection method comprising:
    detecting the target substance by measuring a decrease in or a movement of the optical signal due to a conjugate moving step,
    wherein the conjugate comprises at least the target substance bonding with a magnetic particle, the surface is chemically treated to suppress adsorption of the conjugate, and
    wherein the conjugate moving step is implemented by any one of the steps of:
        a first conjugate moving step of:
            applying, to the conjugate, a first magnetic field in a manner that causes the conjugate to move:
                i) in a direction parallel to the surface, or
                ii) away from the surface, or
                iii) such that orientation of the conjugate changes; and
        a second conjugate moving step of:
            drawing the conjugate on the surface by applying, to the conjugate, a second magnetic field from a magnetic field application unit disposed on a side of a rear face of the sensing plate, and
            moving the magnetic field application unit in a direction having a vector component parallel to an in-plane direction of the surface of the sensing plate while applying the second magnetic field to move the conjugate in accordance with the movement of the magnetic field application unit or change the orientation of the conjugate.

2. The optical detection method according to claim 1, wherein the decrease in the optical signal results from the conjugate moving away from the surface by applying the first magnetic field.

3. The optical detection method according to claim 1, wherein after the conjugate settles out close to the surface due to gravitational sedimentation, the conjugate is moved by the first conjugate moving step.

4. The optical detection method according to claim 1, wherein after the conjugate is drawn close to the surface by applying a drawing magnetic field, the conjugate is moved by the first conjugate moving step.

5. The optical detection method according to claim 4, wherein the step of applying the drawing magnetic field and the first conjugate moving step are alternately conducted a plurality of times.

6. The optical detection method according to claim 1, wherein the conjugate comprises two or more of the magnetic particles bonding with the target substance.

7. The optical detection method according to claim 1, wherein the conjugate comprises the target substance bonding with a labeled substance that emits fluorescence or scattered light in the near field.

8. The optical detection method according to claim 1, wherein the conjugate comprises the target substance bonding with a weight substance.

9. An optical detection device comprising:
    a liquid holding part comprising a sensing plate that can form a near field on a surface with light irradiated from a side of a rear face under a condition of total reflection, the liquid holding part being capable of holding a liquid sample comprising a target substance and a magnetic particle that forms a conjugate with the target substance on the surface of the sensing plate;

a light irradiation unit configured to irradiate light from the side of the rear face of the sensing plate under the condition of total reflection;

a light detection unit disposed on a side which is a front face or a top face of the sensing plate which is located on an opposite side of the rear face of the sensing plate, the light detection unit being configured to detect fluorescence or scattered light emitted from the conjugate at a detection region on the surface and in the near field; and a magnetic field application unit comprising any one of:
- a first magnetic field application unit configured to apply, to the conjugate on the surface of the sensing plate, a first magnetic field that moves the conjugate in a direction parallel to the surface or away from the surface or such that orientation of the conjugate changes, and
- a second magnetic field application unit disposed on the side of the rear face of the sensing plate, wherein the second magnetic field application unit is configured to draw the conjugate in the sample that is introduced on the surface of the sensing plate toward the surface of the sensing plate by applying a second magnetic field that:
  moves the conjugate in a direction having a vector component parallel to an in-plane direction of the surface of the sensing plate, or
  changes orientation of the conjugate while applying the second magnetic field, wherein the surface suppresses adsorption of the conjugate.

10. The optical detection device according to claim 9, wherein the magnetic field application unit comprises the first magnetic field application unit, and comprises a drawing magnetic field application unit configured to apply a drawing magnetic field to draw the conjugate toward the surface.

11. The optical detection device according to claim 9, wherein the light detection unit is a device configured to acquire a state of the detection region comprising the fluorescence or the scattered light as a two-dimensional image.

12. The optical detection device according to claim 9, wherein the sensing plate comprises a laminate structure in which a light-transmissive substrate and a metal layer that generates surface plasmon resonance are stacked in this order from the rear face to the surface.

13. The optical detection device according to claim 9, wherein the sensing plate comprises a laminate structure in which a light-transmissive substrate, a metal layer or a semiconductor layer, and a dielectric layer made of a light-transmissive dielectric material are stacked in this order from the rear face to the surface.

* * * * *